United States Patent
Stranix et al.

(10) Patent No.: US 8,664,248 B2
(45) Date of Patent: *Mar. 4, 2014

(54) DERIVATIVES OF PYRIDOXINE FOR INHIBITING HIV INTEGRASE

(75) Inventors: Brent Richard Stranix, Pointe-Claire (CA); Guy Milot, Toronto (CA); Jean-Emmanuel Bouchard, Quebec (CA)

(73) Assignee: TaiMed Biologics, Inc., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/605,502

(22) Filed: Sep. 6, 2012

(65) Prior Publication Data

US 2012/0329827 A1 Dec. 27, 2012

Related U.S. Application Data

(62) Division of application No. 13/004,533, filed on Jan. 11, 2011, now Pat. No. 8,283,366.

(60) Provisional application No. 61/297,450, filed on Jan. 22, 2010.

(51) Int. Cl.
*A61K 31/44* (2006.01)
*C07D 213/62* (2006.01)
*C07D 213/78* (2006.01)

(52) U.S. Cl.
USPC ........... 514/350; 514/351; 546/298; 546/299; 546/300

(58) Field of Classification Search
None
See application file for complete search history.

(56) References Cited

U.S. PATENT DOCUMENTS

| | | | |
|---|---|---|---|
| 6,110,716 A | 8/2000 | Lingham et al. | |
| 6,124,327 A | 9/2000 | Silverman et al. | |
| 6,245,806 B1 | 6/2001 | Dombrowski et al. | |
| 6,262,055 B1 | 7/2001 | Young et al. | |
| 6,271,402 B1 | 8/2001 | Singh et al. | |
| 6,306,891 B1 | 10/2001 | Selnick et al. | |
| 6,310,211 B1 | 10/2001 | Vaillancourt et al. | |
| 6,380,249 B1 | 4/2002 | Young et al. | |
| 6,395,743 B1 | 5/2002 | Heimbuch et al. | |
| 6,403,347 B1 | 6/2002 | Bills et al. | |
| 6,506,786 B2 | 1/2003 | Stranix et al. | |
| 6,528,532 B1 | 3/2003 | Stranix et al. | |
| 6,541,515 B2 | 4/2003 | Singh et al. | |
| 6,548,546 B2 | 4/2003 | Walker et al. | |
| 6,608,100 B1 | 8/2003 | Stranix et al. | |
| 6,610,689 B2 | 8/2003 | Stranix et al. | |
| 6,632,816 B1 | 10/2003 | Stranix et al. | |
| 6,656,965 B2 | 12/2003 | Stranix et al. | |
| 6,677,367 B2 | 1/2004 | Stranix et al. | |
| 6,777,440 B2 | 8/2004 | Walker et al. | |
| 6,803,378 B2 | 10/2004 | Walker et al. | |
| 6,919,351 B2 | 7/2005 | Anthony et al. | |
| 7,037,908 B2 | 5/2006 | Naidu et al. | |
| 7,109,186 B2 | 9/2006 | Walker et al. | |
| 7,115,601 B2 | 10/2006 | Naidu et al. | |
| 7,135,467 B2 | 11/2006 | Walker et al. | |
| 7,232,819 B2 | 6/2007 | Di Francesco et al. | |
| 7,253,180 B2 | 8/2007 | Chen et al. | |
| 7,279,487 B2 | 10/2007 | Egbertson et al. | |
| 7,388,008 B2 | 6/2008 | Stranix et al. | |
| 7,435,734 B2 | 10/2008 | Crescenzi et al. | |
| 7,459,452 B2 | 12/2008 | Di Francesco et al. | |
| 7,476,666 B2 | 1/2009 | Wai et al. | |
| 7,538,112 B2 | 5/2009 | Wai et al. | |
| 8,008,297 B2 | 8/2011 | Stranix et al. | |
| 8,283,366 B2 * | 10/2012 | Stranix et al. | 514/346 |
| 2001/0014748 A1 | 8/2001 | Singh et al. | |
| 2003/0027847 A1 | 2/2003 | Walker et al. | |

(Continued)

FOREIGN PATENT DOCUMENTS

| | | |
|---|---|---|
| WO | WO 98/34932 | 8/1998 |
| WO | WO 99/62513 | 12/1999 |

(Continued)

OTHER PUBLICATIONS

Parkin, JM. et al. Tolerability and side-effects of post-exposure prophylaxis for HIV infection. The Lancet. 2000, vol. 355, p. 722, first paragraph.*

(Continued)

*Primary Examiner* — Janet L Andres
*Assistant Examiner* — Ben S Michelson
(74) *Attorney, Agent, or Firm* — Clark & Elbing LLP

(57) ABSTRACT

The present invention relates to methods of treating hepatitis C infection, HIV infection, AIDS, or AIDS-related complex, or inhibiting HIV replication by administering a compound of Formula I

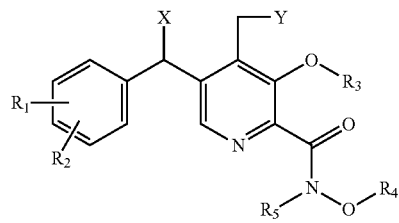

wherein:
X is H or OH;
Y is H or OH;
$R_1$ is H or halogen (F, Cl, Br, I);
$R_2$ is H or halogen (F, Cl, Br, I);
$R_3$ is H, $C_{1-6}$ alkyl, $C_{1-6}$ fluoroalkyl, or benzyl;
$R_4$ is H, $C_{1-6}$ alkyl, or benzyl; and
$R_5$ is H or $C_{1-6}$ alkyl;
or pharmaceutically acceptable salts thereof, to a mammal.

7 Claims, No Drawings

(56) References Cited

U.S. PATENT DOCUMENTS

| | | |
|---|---|---|
| 2004/0110804 A1 | 6/2004 | Walker et al. |
| 2005/0043370 A1 | 2/2005 | Walker et al. |
| 2005/0261322 A1 | 11/2005 | Naidu et al. |
| 2006/0025592 A1 | 2/2006 | Stranix et al. |
| 2006/0211724 A1 | 9/2006 | Verschueren et al. |
| 2007/0111984 A1 | 5/2007 | Naidu et al. |
| 2007/0124152 A1 | 5/2007 | Johns et al. |
| 2007/0129379 A1 | 6/2007 | Naidu et al. |
| 2007/0161639 A1 | 7/2007 | Jones et al. |
| 2007/0179196 A1 | 8/2007 | Han et al. |
| 2008/0015187 A1 | 1/2008 | Wai et al. |
| 2008/0139579 A1 | 6/2008 | Morrissette et al. |
| 2008/0194523 A1 | 8/2008 | Johns et al. |
| 2008/0214503 A1 | 9/2008 | Johns et al. |
| 2008/0214527 A1 | 9/2008 | Kawasuji et al. |
| 2008/0234231 A1 | 9/2008 | Johns et al. |
| 2008/0306051 A1 | 12/2008 | Naidu et al. |
| 2009/0099168 A1 | 4/2009 | Donghi et al. |
| 2009/0253677 A1 | 10/2009 | Beaulieu et al. |
| 2009/0312335 A1 | 12/2009 | Wai et al. |
| 2010/0087419 A1 | 4/2010 | Isaacs et al. |
| 2010/0184028 A1 | 7/2010 | Hsing et al. |
| 2010/0184974 A1 | 7/2010 | Stranix et al. |
| 2010/0216834 A1 | 8/2010 | Isaacs et al. |
| 2011/0178120 A1 | 7/2011 | Stranix et al. |
| 2011/0184028 A1 | 7/2011 | Stranix et al. |
| 2011/0245241 A1 | 10/2011 | Naidu et al. |
| 2011/0257621 A1 | 10/2011 | Fangrow et al. |
| 2011/0275621 A1 | 11/2011 | Vacca et al. |

FOREIGN PATENT DOCUMENTS

| | | |
|---|---|---|
| WO | WO 99/62520 | 12/1999 |
| WO | WO 01/27309 | 4/2001 |
| WO | WO 01/96283 | 12/2001 |
| WO | WO 01/98248 | 12/2001 |
| WO | WO 03/049690 | 6/2003 |
| WO | WO 2004/062613 | 7/2004 |
| WO | WO 2004/096128 | 11/2004 |
| WO | WO 2004/096807 | 11/2004 |
| WO | WO 2005/077050 | 8/2005 |
| WO | WO 2005/086700 | 9/2005 |
| WO | WO 2005/087766 | 9/2005 |
| WO | WO 2005/092099 | 10/2005 |
| WO | WO 2006/103399 | 10/2005 |
| WO | WO 2005/110414 | 11/2005 |
| WO | WO 2007/019098 | 2/2007 |
| WO | WO 2007/019100 | 2/2007 |
| WO | WO 2007/019101 | 2/2007 |
| WO | WO 2007/050510 | 5/2007 |
| WO | WO 2007/059125 | 5/2007 |
| WO | WO 2007/059229 | 5/2007 |
| WO | WO 2007/061714 | 5/2007 |
| WO | WO 2008/002959 | 1/2008 |
| WO | WO 2009/146555 | 12/2009 |
| WO | WO 2010/122980 | 10/2010 |
| WO | WO 2011/046873 | 4/2011 |

OTHER PUBLICATIONS

Freshney, RI. Culture of Animal Cells: A Manual of Basic Technique. John Wiley and Sons. 2000, 4th Ed., p. 4.*

Dermer, GB. Another Anniversary for the War on Cancer. Bio/Technology. 1994, vol. 12, p. 320.*

Weeks, BS. et al. AIDS: The Biological Basis. 4th Ed., 2006, p. 91, first paragraph.*

West, AR. Solid State Chemistry and its Applications. John Wiley and Sons, LTD. 1990, p. 358 and p. 365.*

International Search Report for International Application No. PCT/CA2011/000041, dated Apr. 6, 2011 (5 pages).

Parkin et al., "Tolerability and side-effects of post-exposure prophylaxis for HIV infection," *Lancet* 355(9205): 722-723 (2000).

Freshney, *Culture of Animal Cells: A Manual of Basic Technique*, 4th edition, New York: Wiley-Liss, pp. 4-6 (2000).

Weeks et al., *AIDS: The Biological Basis*, 4th edition, Sudbury, MA: Jones and Bartlett Publishers, pp. 91-93 (2006).

Dermer, "Another anniversary for the war on cancer," *Biotechnology* 12: 320 (1994).

West, "Solid Solutions," Chapter 10 in *Solid State Chemistry and Its Applications*, New York: John Wiley and Sons, Ltd., pp. 358-359, and 365 (1990).

* cited by examiner

DERIVATIVES OF PYRIDOXINE FOR INHIBITING HIV INTEGRASE

CROSS-REFERENCE TO RELATED APPLICATIONS

This application claims benefit of U.S. Provisional Application No. 61/297,450, filed Jan. 22, 2010, which is hereby incorporated by reference.

FIELD OF THE INVENTION

The present invention is directed to pyridoxine (vitamin $B_6$) derived compounds of Formula I, pharmaceutically acceptable salts or solvates thereof, pharmaceutical formulations comprising one or more compounds of Formula I, their synthesis, and use as modulators or inhibitors of human immunodeficiency virus (HIV) integrase enzyme. Compounds of the present invention are useful for prophylaxis, treatment, delay in the onset or delay in the progression of human immuno-deficiency virus (HIV) infection, acquired immune deficiency syndrome AIDS, AIDS-related complex (ARC), and other diseases and conditions caused or mediated by HIV infection.

BACKGROUND OF THE INVENTION

Retroviruses designated as human immunodeficiency virus (HIV), particularly strains known as HIV-1 and HIV-2, are the etiological agent of AIDS, ARC, and other diseases or conditions caused or mediated by HIV. HIV infection and AIDS are difficult to treat due to the ability of retroviruses to rapidly replicate, mutate and acquire drug resistance. To date, the treatment of AIDS and HIV infection and the development of new drugs for AIDS and HIV infection have focused primarily on the inhibition of HIV replication by targeting key steps in retroviral replication, such as conversion of viral RNA to viral DNA (reverse transcription) and insertion (integration) of viral DNA into the host genome. These steps rely on the activity of HIV enzymes including reverse transcriptase, protease and integrase. Various synthetic antiviral agents that block various stages of the HIV replication cycle have been developed and marketed including compounds that: interfere with viral binding to CD4 (+) T-lymphocytes (for example, soluble CD4), block viral reverse transcriptase (for example, didanosine and zidovudine (AZT)), block viral aspartyl protease (for example Ritonavir and Indinavir) and inhibit virion budding (for example interferon). Some of these agents have proved ineffective in clinical tests and others, primarily those that target the early stages of viral replication, have no effect on the production of infectious virions in chronically infected cells. Furthermore, administration of therapeutic doses of these agents has commonly led to cell-toxicity, unwanted side effects, such as anemia, neurotoxicity and bone marrow suppression, and rapid emergence of drug resistance which limits safe and effective treatment of AIDS, HIV infection and other HIV-caused diseases.

The use of combination therapy has suppressed the emergence of resistance relative to monotherapy, however even with combination therapy there is a loss of efficacy in 30-50% of patients due to the development of viral resistance. Considering the shortcomings of reverse transcriptase and protease inhibitors, even when used as part of a drug cocktail (combination therapy), there is a need for new antiviral drugs and in particular drugs that do not lead to cross-resistance with the current standard of care.

SUMMARY OF THE INVENTION

The compounds of the present invention are useful for inhibiting or modulating HIV integrase enzyme activity and, in particular, for inhibiting HIV replication and for treating HIV infection, AIDS, and HIV-mediated diseases and conditions. The present invention relates to a series of integrase inhibitors derived from pyridoxine and pharmaceutically acceptable derivatives thereof (e.g., salts and solvates).

In one aspect the present invention are compounds of formula I,

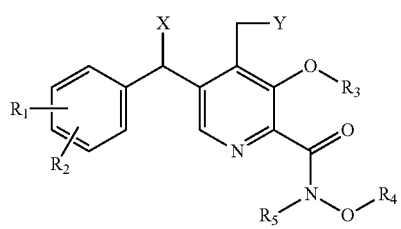

wherein:
   X is H or OH;
   Y is H or OH;
   $R_1$ is H or halogen (F, Cl, Br, I);
   $R_2$ is H or halogen (F, Cl, Br, I);
   $R_3$ is H, $C_{1-6}$ alkyl, $C_{1-6}$ fluoroalkyl, or benzyl;
   $R_4$ is H, $C_{1-6}$ alkyl, or benzyl; and
   $R_5$ is H, or $C_{1-6}$ alkyl; or
pharmaceutically acceptable salts or solvates thereof.

Further provided herein are compounds of formula Ia,

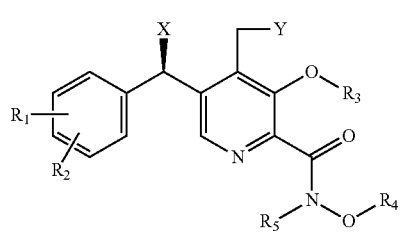

wherein:
   X is OH;
   Y is H or OH;
   $R_1$ is H or halogen (F, Cl, Br, I);
   $R_2$ is H or halogen (F, Cl, Br, I);
   $R_3$ is H, $C_{1-6}$ alkyl or benzyl;
   $R_4$ is H, $C_{1-6}$ alkyl or benzyl; and
   $R_5$ is H or $C_{1-6}$ alkyl; or
pharmaceutically acceptable salts or solvates thereof.

Further provided herein are compounds of formula Ib,

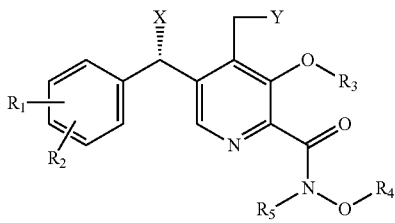

wherein:
X is OH;
Y is H or OH;
R$_1$ is H or halogen (F, Cl, Br, I);
R$_2$ is H or halogen (F, Cl, Br, I);
R$_3$ is H, C$_{1-6}$ alkyl or benzyl;
R$_4$ is H, C$_{1-6}$ alkyl or benzyl; and
R$_5$ is H, C$_{1-6}$ alkyl or benzyl; or
pharmaceutically acceptable salts or solvates thereof.
Further provided herein are compounds of formula Ic:

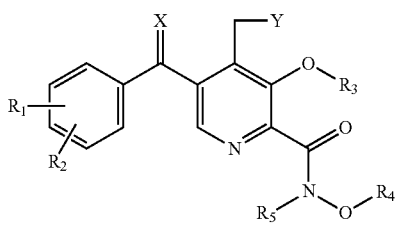

wherein:
X is O or N—OH;
Y is H or OH;
R$_1$ is H or halogen (F, Cl, Br, I);
R$_2$ is H or halogen (F, Cl, Br, I);
R$_3$ is H, C$_{1-6}$ alkyl or benzyl;
R$_4$ is H, C$_{1-6}$ alkyl or benzyl; and
R$_5$ is H, C$_{1-6}$ alkyl or benzyl; or
pharmaceutically acceptable salts or solvates thereof.

Further provided herein are compounds of formula I selected from N5-(4-fluorobenzyl)-N2,3-dihydroxy-4-(hydroxymethyl)pyridine-2,5-dicarboxamide, N5-(3-chloro-4-fluorobenzyl)-N2,3-dihydroxy-4-(hydroxymethyl)pyridine-2,5-dicarboxamide, N5-(3,4-dichlorobenzyl)-N2,3-dihydroxy-4-(hydroxymethyl)pyridine-2,5-dicarboxamide, and 5-(benzyloxymethyl)-N,3-dihydroxy-4-(hydroxymethyl)picolinamide.

Further provided herein are compounds selected from (R)-5-(3-Chloro-4-fluorophenyl) (hydroxy)methyl)-N,3-dihydroxy-4-(hydroxymethyl)picolinamide; 5-(4-fluorobenzyl)-N,3-dihydroxy-4-(hydroxymethyl)picolinamide; 5-((4-fluorophenyl) (hydroxy)methyl)-N,3-dihydroxy-4-(hydroxymethyl)picolinamide; 5-((4-fluorophenyl) (hydroxy)methyl)-N-hydroxy-N,2,2-trimethyl-4H-[1,3]dioxino[4,5-c]pyridine-8-carboxamide; 5-((4-fluorophenyl) (hydroxy)methyl)-N,3-dihydroxy-4-(hydroxymethyl)-N-methylpicolinamide; 5-((4-fluorophenyl)(hydroxy)methyl)-3-hydroxy-4-(hydroxymethyl)-N-methoxypicolinamide; 5-(4-fluorobenzyl)-N,3-dihydroxy-4-methylpicolinamide; 5-((4-fluorophenyl)(hydroxy)methyl)-N,3-dihydroxy-4-methylpicolinamide; 5-(4-fluorobenzoyl)-N,3-dihydroxy-4-methylpicolinamide; (E)-5-((4-fluorophenyl)(hydroxyimino)methyl)-N,3-dihydroxy-4-methylpicolinamide; and (S)-5-((3-Chloro-4-fluorophenyl)(hydroxy)methyl)-N,3-dihydroxy-4-(hydroxymethyl)picolinamide.

Further provided herein are pharmaceutical compositions, and pharmaceutically acceptable formulations, comprising a therapeutically effective amount of at least one compound of the present invention, and pharmaceutically acceptable salts or solvates thereof.

The compounds of the present invention inhibit HIV integrase including both HIV-1 and HIV-2 and may be used as antiviral agent against HIV, including HIV-1 and HIV-2 strains.

The compounds of the present invention are useful for prophylaxis, treatment or delay in the onset or progression of HIV infection, or of a disease or condition caused or mediated by HIV infection, including HIV-1 and HIV-2 infection.

In one aspect, the present invention features a method of inhibiting HIV replication, in a mammal, that includes administering to the mammal a replication-inhibiting amount of at least one compound of the present invention, or a pharmaceutically acceptable salt or solvate thereof.

Further provided are methods of inhibiting HIV replication in a cell, comprising contacting the cell with an inhibiting amount of at least one compound of the present invention, or a pharmaceutically acceptable salt, solvate or formulation thereof.

Further provided are methods of inhibiting HIV integrase enzyme activity, comprising contacting the integrase enzyme with an integrase-inhibiting amount of at least one compound of the present invention, or a pharmaceutically acceptable salt, solvate or formulation thereof. The method includes contacting a cell directly or administering the compound of the invention to a mammal suffering from an HIV infection.

Another aspect of the present invention includes methods of treating HIV infection in a mammal, comprising administering to the mammal at least one compound of the present invention, or a pharmaceutically acceptable salt, solvate or formulation thereof.

Further provided are methods of treating AIDS in a mammal, comprising administering to the mammal at least one compound of the present invention, or a pharmaceutically acceptable salt, solvate or formulation thereof.

Further provided are methods of treating AIDS in a mammal, comprising administering to the mammal at least one compound of the present invention, or a pharmaceutically acceptable salt, solvate or formulation thereof in combination with one or more additional HIV-inhibiting agent.

Further provided are methods of treating a disease or condition caused or mediated by HIV infection in a mammal, comprising administering to the mammal at least one compound of the present invention, or a pharmaceutically acceptable salt, solvate or formulation thereof.

Further provided are methods of prophylaxis or prevention of HIV infection in a mammal, comprising administering to the mammal at least one compound of the present invention, or a pharmaceutically acceptable salt, solvate or formulation thereof.

Further provided are methods of inhibiting HIV replication in a mammal comprising administering to the mammal at least one compound of the present invention or a pharmaceutically acceptable salt, solvate or formulation thereof.

Further provided are methods of inhibiting HIV replication in a mammal comprising administering to the mammal at least one compound of the present invention, or a pharmaceutically acceptable salt, solvate or formulation thereof and at least one other HIV-inhibiting agent.

Further provided are methods of inhibiting HIV replication in a mammal wherein the HIV is resistant to at least one HIV protease inhibitor, the method comprising administering to the mammal at least one compound of the present invention, or a pharmaceutically acceptable salt, solvate or formulation thereof.

Further provided are methods of inhibiting HIV replication in a mammal, having an HIV infection, wherein the HIV is resistant to at least one HIV reverse transcriptase inhibitor, the method comprising administering to the mammal at least one compound of the present invention, or a pharmaceutically acceptable salt, solvate or formulation thereof.

Further provided are methods of reducing HIV viral load in a mammal infected with HIV, comprising administering to the mammal at least one compound of the present invention, or a pharmaceutically acceptable salt, solvate or formulation thereof.

Further provided are methods of reducing HIV viral load in a mammal infected with HIV, comprising administering to the mammal at least one compound of the present invention, or a pharmaceutically acceptable salt, solvate or formulation thereof in combination with one or more additional HIV-inhibiting agents.

Further provided is the use of at least one compound of the present invention for the manufacture of a pharmaceutical composition for treatment of HIV infection.

Further provided is the use of at least one compound of the present invention for the manufacture of a pharmaceutical composition for treatment of AIDS or ARC.

Further provided is the use of at least one compound of the present invention for the manufacture of a pharmaceutical composition for prevention or prophylaxis of AIDS or ARC.

Further provided is the use of at least one compound of the present invention for the manufacture of a pharmaceutical composition for prevention or prophylaxis of HIV infection.

For any of the above aspects of the invention, the mammal (e.g., human) may have or be suspected of having an HIV infection or an AIDS or HIV mediated disease or condition. The mammal (e.g., human) may or may not have been previously treated with anti-viral or other therapeutic compounds for the HIV infection or AIDS or HIV mediated disease or condition.

DEFINITIONS

The terms "human immunodeficiency virus," "HIV," "HIV-1," or "HIV-2" as used herein refer to a retrovirus that is the causative agent for acquired immunodeficiency Syndrome (AIDS) and diseases, conditions or opportunistic infections associated with AIDS. Previous names for HIV include human T-lymphotropic virus-III (HTLV-III), lymphadenopathy-associated virus (LAV), and AIDS-associated retrovirus (ARV).

The terms "HIV reverse transcriptase," "reverse transcriptase," or "RT" as used herein refer to an enzyme, encoded by a retroviral genome, which catalyzes or mediates the conversion (reverse transcription) of viral RNA to DNA or generation of a provirus (Haseltine W. A. FASEB J. vol. 5, p. 2349-2360 (1991)).

The terms "reverse transcriptase inhibitor" or "HIV reverse transcriptase inhibitor," as used herein, refer to compounds or combinations of compounds that interfere with the proper functioning of the HIV reverse transcriptase enzyme that is responsible for converting single-stranded HIV viral RNA into HIV viral DNA.

The terms "HIV integrase" or "integrase" as used herein refer to an enzyme, encoded by a retroviral genome, that catalyzes or mediates integration of provirus DNA (retroviral double stranded DNA) into the host genomic DNA. The integrase enzyme can serve as a template for viral gene expression by the host transcription system, leading to viral replication (Roth et al., Cell, 1989 Jul. 14; 58(1):47-54.: Bukrinsky M. I., Proc. Natn. Acad. Sci. USA 1992, vol. 89 p. 6580-6584; Gallay et al., Cell. 1995 Nov. 17; 83(4):569-76).

The terms "integrase inhibitor" or "HIV integrase inhibitor," as used herein, refer to a compound or combination of compounds that interfere with the proper functioning of the HIV integrase enzyme that is responsible for inserting the genes of HIV into the DNA of a host cell.

The term "integration" as used herein refers to insertion of viral DNA, retroviral DNA, provirus, or provirus DNA into the host genome mediated by integrase enzyme. Integration generally occurs following association of integrase and viral DNA with the pre-integration complex (PIC) at the host nucleus and transport of the viral DNA into the host nucleus as a component of the pre-integration complex (Goldgur Y et al Proc Natl Acad Sci U S A. 1999 Nov. 9; 96(23):13040-3; Sayasith K, Sauvé G and Yelle J. Expert Opin Ther Targets. 2001 August;5(4):443-464; Debyser Z et al Methods Mol Biol. 2001;160:139-55).

The terms "protease inhibitor" or "HIV protease inhibitor" as used herein mean compounds or combinations of compounds that interfere with the proper functioning of the HIV protease enzyme that is responsible for cleaving long strands of viral protein into the separate proteins making up the viral core.

The terms "fusion inhibitor" or "HIV fusion inhibitor," as used herein, refer to compounds or combinations of compounds that bind to the gp41 envelope protein on the surface of CD4 cells and block the structural changes necessary for the virus to fuse with the cell.

The terms "viral load" and "HIV viral load," as used herein, mean the amount of HIV in the circulating blood of a mammal, such as a human. The amount of HIV virus in the blood of mammal can be determined by measuring the quantity of HIV RNA in the blood using methods known to those of ordinary skill in the art.

The term "retrovirus" as used herein refers to a virus belonging to the viral family Retroviridae, which includes viruses that possess an RNA genome, and that replicate via a DNA intermediate.

The term "Vitamin $B_6$" as used herein refers to one or more of three compounds that are commonly referred to as vitamin $B_6$ namely pyridoxal, pyridoxamine and pyridoxine. Pyridoxine differs from pyridoxamine by the substituent at the 4' position. Pyridoxine based on a pyridine ring, with hydroxyl, methyl, and hydroxymethyl substituents and is converted in vivo to pyridoxal 5-phosphate, the biologically active form of pyridoxine.

The terms "comprising" and "including" are used in their open, non-limiting sense.

The term "$C_{1-6}$ alkyl" as used herein means saturated monovalent hydrocarbon radicals having straight or branched moieties and containing from 1 to 6 carbon atoms. The $C_{1-6}$ alkyl group may be substituted or unsubstituted. Examples of such groups include, but are not limited to, methyl, ethyl, propyl, iso-propyl, n-butyl, iso-butyl, and tert-butyl.

As used herein, the terms "benzyl" and "phenyl" refer to both substituted and unsubstitued benzyl and phenyl groups, respectively.

The term "fluoroalkyl," as used herein, represents a $C_{1-6}$ alkyl group, as defined herein, where one or more hydrogen radicals bound to the alkyl group has been replaced by a fluoride radical. A fluoroalkyl group can be further substituted with any of the substituent groups described herein for $C_{1-6}$ alkyl groups. Fluoroalkyl groups are exemplified by trifluoromethyl, pentafluoroethyl, and the like.

Where a group (e.g., a $C_{1-6}$ alkyl group, benzyl, or phenyl group) is substituted, the group may be substituted with, e.g., 1, 2, 3, 4, 5, or 6 substituents. Optional substituents for $C_{1-6}$ alkyl groups include, but are not limited to: $C_{3-9}$ cycloalkyl, $C_{3-9}$ cycloalkenyl, a heterocyclyl having 3-9 ring atoms, a heteroaryl having 5-12 ring atoms, azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O)OR'), hydroxy (—OH), isocyano (—NC), sulfonate (—S(=O)$_2$R), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, $C_{3-9}$ cycloalkyl, a heterocyclyl having 3-9 ring atoms, $C_{6-10}$ aryl, or a heteroaryl having 5-12 ring atoms. Optional substituents for phenyl or benzyl groups include, but are not limited to, the optional substituents described herein for alkyl groups, as well as $C_{1-6}$ alkyl, $C_{2-6}$ alkenyl, $C_{2-6}$ alkynyl, $C_{6-10}$ aryl, and halogen (e.g., F, Cl, Br, or I) substituents.

The term "inhibiting HIV replication" means reducing or preventing (e.g., by at least 10%, 20% 30%, 40%, 50%, 60%, 70%, 80%, 90% or more) human immunodeficiency virus (HIV) replication in a cell. Such a cell may be present in vitro, or it may be present in vivo, such as in a mammal, such as a human. Such inhibition may be accomplished by administering a compound of the present invention, or a pharmaceutically acceptable salt or solvate thereof, directly to the cell, or to a mammal, in an amount sufficient to inhibit HIV replication. The inhibition of HIV replication in a cell, such as in a mammal, can be measured or monitored using methods known to those of ordinary skill in the art. For example, an amount of a compound of the invention may be administered to a mammal, either alone or as part of a pharmaceutically acceptable formulation. Blood samples may then be withdrawn from the mammal and the amount of HIV virus in the sample may be quantified using methods known to those of ordinary skill in the art. A reduction in the amount of HIV virus in the sample compared to the amount found in the blood before administration of a compound of the invention would represent inhibition of the replication of HIV virus in the mammal. In another example, a reduction in the amount of HIV virus in the sample compared to the amount found in a positive reference sample (e.g., the blood from a subject having HIV but not treated with a compound of the invention) would represent inhibition of the replication of HIV virus in the mammal. The administration of a compound of the invention to the cell, such as in a mammal, may be in the form of single dose or a series of doses. In the case of more than one dose, the doses may be administered in one day or they may be administered over more than one day.

The terms "HIV-inhibiting agent," "HIV antiviral agent," or "anti-HIV agent" as used herein means a compound, including but not limited to the compounds of the present invention, or a pharmaceutically acceptable salt thereof which is capable of inhibiting the replication of HIV in a cell, such as a cell in a mammal. Such compounds may inhibit HIV replication through any mechanism known to those of ordinary skill in the art. Non-limiting examples of HIV-inhibiting agents include an entry inhibitor, a protease inhibitor, a reverse transcriptase inhibitor, a fusion inhibitor, and an integrase inhibitor.

The terms "human immunodeficiency virus-inhibiting amount" or "HIV-inhibiting amount," as used herein, refer to the amount of an HIV-inhibiting agent, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods described herein and those known to those of ordinary skill in the art.

The term "inhibiting HIV integrase enzyme activity," as used herein, means decreasing (e.g., by at least 10%, 20% 30%, 40%, 50%, 60%, 70%, 80%, 90% or more) the activity or functioning of the HIV integrase enzyme either in vitro or in vivo, such as in a mammal, such as a human.

The term "HIV integrase enzyme-inhibiting amount," as used herein, refers to the amount of an HIV-inhibiting agent or a pharmaceutically acceptable salt or solvate thereof, required to decrease the activity of the HIV integrase enzyme either in vivo, such as in a mammal, or in vitro, such as in a cultured cell line. In one example, such inhibition may take place by the compound of the present invention binding directly to the HIV integrase enzyme. In addition, the activity of the HIV integrase enzyme may be decreased in the presence of a compound of the present invention when such direct binding between the enzyme and the compound does not take place. Furthermore, such inhibition may be competitive, non-competitive, or uncompetitive. Inhibition of HIV integrase may be determined using in vitro or in vivo systems, or a combination of both, using methods known to those of ordinary skill in the art.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof In one embodiment of the present invention, one solvent molecule is associated with one molecule of the compounds of the present invention, such as a hydrate. In another embodiment of the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention include solvates of compounds of the present invention that retain the biological effectiveness of the non-hydrate form of the compounds.

A "pharmaceutically acceptable salt" as used herein means a salt that retains the biological effectiveness of the free acids and bases of the specified derivative, containing pharmacologically acceptable anions or cations, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1, 4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, y-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, valerate salts, and cations, such as sodium, potassium, calcium, magnesium, ammonium, and tetraalkylammonium, among others.

The term "pharmaceutically acceptable formulation," as used herein, means a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as keolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional anti-HIV agents. A pharmaceutically acceptable formulation may also include but is not limited to compounds, other than the compounds of formula 1, having a structure such that, upon administration to a recipient or patient, a compound of this invention, active metabolite or residue thereof is directly or indirectly provided.

By "reduce" or "inhibit" is meant the ability to cause an overall decrease of 10%, 20% 30%, 40%, 50%, 60%, 70%, 80%, 90% or more in the biological activity or levels being measured.

The term "therapeutically effective amount," as used herein, means an amount of a compound of the present invention, or a pharmaceutically acceptable salt thereof, that, when administered to a mammal in need of such treatment, is sufficient to effect treatment, as defined herein. Thus, a therapeutically effective amount of a compound of the present invention, or a pharmaceutically acceptable salt thereof, is a quantity sufficient to modulate or inhibit the activity of the HIV integrase enzyme such that a disease condition that is mediated by activity of the HIV integrase enzyme is reduced or alleviated.

The terms "treat," "treating," or "treatment" refers to both therapeutic treatment and prophylactic or preventative measures for an HIV infection or an HIV or AIDS mediated disease or condition. To "treat disease" or use for "therapeutic treatment" refers to administering treatment to a subject already suffering from a disease to improve the subject's condition. Treatment can include modulating or inhibiting the disease or condition, (e.g., arresting its development); relieving the disease or condition, (e.g., causing regression of the disease or condition); reduction in viral load; or relieving and/or alleviating the disease or condition or the symptoms resulting from the disease or condition with or without addressing the underlying disease or condition. To "prevent disease" refers to prophylactic treatment of a subject who is not yet ill, but who is susceptible to, or otherwise at risk of, developing a particular disease. Prophylactic treatment can also include the prevention of one or more symptoms associated with HIV or AIDS. Thus, in the claims and embodiments, treating includes the administration to a mammal either for therapeutic or prophylactic purposes.

By "subject" is meant a mammal, including, but not limited to, a human or non-human mammal, such as a simian, bovine, canine, equine or feline.

The terms "resistant," "resistance," and "resistant HIV," as used herein, refer to HIV virus demonstrating a reduction in sensitivity to a particular drug. A mammal infected with HIV that is resistant to a particular anti-HIV agent or combination of agents usually manifests an increase in HIV viral load despite continued administration of the agent or agents. Resistance may be either genotypic, meaning that a mutation in the HIV genetic make-up has occurred, or phenotypic, meaning that resistance is discovered by successfully growing laboratory cultures of HIV virus in the presence of an anti-HIV agent or a combination of such agents.

The terms "co-administration," "co-administering," "co-administer," "co-administered," or "combination therapy" as used herein, refer to the administration of a combination of at least a first agent and a second agent and can include two or more agents. Such co-administration can be performed such that two or multiple agents are part of the same composition or part of the same unitary dosage form, or in separate compositions or dosage forms. Co-administration also includes administering a first agent and a second agent, or more than two agents separately and as part of the same therapeutic regimen. The agents, if administered separately, need not necessarily be administered at essentially the same time, although they can be if so desired. Thus, co-administration includes, for example, administering a first agent and a second agent as separate dosages or dosage forms, but at the same time. Co-administration also includes separate administration at different times (e.g., sequentially or alternating one agent with the other) and in any order.

The term "compound of the present invention" refers to compounds of formulas I and Ia, Ib, and Ic as well compounds provided in the Examples that follow, and includes pharmaceutically acceptable salts of these compounds.

The abbreviations used herein refer to the following:

| Abbreviation | Meaning |
| --- | --- |
| AcOH | Acetic acid |
| Ar | Argon |
| AIDS | Acquired Immunodeficiency Syndrome |
| AZT | 3-Azido-3-deoxythymine (Zidovudine) |
| BSA | Bovine serum albumin |
| DMF | Dimethylformamaide |
| DNA | Deoxyribonucleic acid |
| EtOH | Ethyl alcohol |

-continued

| Abbreviation | Meaning |
| --- | --- |
| g | gram |
| HPLC | High pressure liquid chromatography |
| HIV-1, -2 | Human immunodeficiency virus type 1, type 2 |
| HTLV-I, -II | Human T-cell lymphotropic virus type I, type II |
| M | Molar |
| MeOH | Methyl alcohol |
| mg | Milligram |
| mp | Melting point |
| min | Minute |
| mL | Milliliter |
| mmol | Millimole |
| nM | Nanomolar |
| RNA | Ribonucleic acid |
| RBF | Round bottomed flask |
| THF | Tetrahydrofuran |

DETAILED DESCRIPTION

Pharmaceutical compositions contemplated herein comprise at least one compound of the present invention, including pharmaceutically acceptable salts, solvate or formulations thereof, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol, liposomes and lanolin.

It is understood by those skilled in the art that the compounds of the present invention, salts, or solvates thereof may exist in different crystal or polymorphic forms that are within the scope of the present invention and specified formulas.

Compounds of the present invention that are basic may be prepared as a salt using suitable methods known in the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

Basic compounds of the present invention can form a variety of salts with various inorganic and organic acids. Although such salts must be pharmaceutically acceptable for administration to animals, it is common practice to first isolate the compound of the present invention as a pharmaceutically unacceptable salt and then convert to a free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol.

Compounds of the present invention that are acidic may be prepared as a salt using suitable methods known in the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

Acidic compounds of the present invention can form base salts with various pharmacologically acceptable cations. Examples of such salts include the alkali metal or alkaline-earth metal salts and particularly, the sodium and potassium salts, which can be prepared using conventional techniques. The chemical bases suitable as reagents in preparing the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

To treat or prevent diseases or conditions caused or mediated by HIV, a pharmaceutical composition, comprising at least one of the compounds of the present invention, is administered in a pharmaceutically acceptable formulation prepared by combining a therapeutically effective amount of the compound with one or more pharmaceutically suitable carriers including diluents, excipients and auxiliaries that facilitate processing of the active compounds into a pharmaceutically acceptable formulation. Carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such: as Labrasol®, Gelucire® or the like, or formulator, such as CHIC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0-60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Pharmaceutical preparations for oral use can be obtained using a solid excipient in an admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

The pharmaceutical compositions, comprising the compounds of the present invention may also contain suitable solid- or gel-phase carriers or excipients. These carriers and excipients may provide marked improvement in the bioavailability of poorly soluble drugs. Examples of such carriers or excipients include calcium carbonate, calcium, phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used. Further, the pharmaceutical composition may be incorporated into a skin patch for delivery of the drug directly onto the skin.

Methods of prophylaxis and treatment, their dosage levels and requirements may be selected by those of ordinary skill in the art from available methods and techniques.

The compounds of this invention may be modified by appending appropriate functionalities to enhance selective biological properties. Such modifications are known in the art and include those which increase biological penetration into a given biological system (e.g., blood, lymphatic system, central nervous system), increase oral bioavailability, increase solubility to allow administration by injection, alter metabolism or alter rate of excretion (*Pharmacokinetic Optimization in Drug Research*, Testa, B. et al, 2001, Wiley-VCH, VCHA).

The pharmaceutical compositions of this invention may be administered orally, intravenously, parenterally, by inhalation spray, topically, rectally, nasally, buccally, vaginally, or via an implanted reservoir and are preferably administered orally or parenterally. The pharmaceutical compositions of this invention may contain any conventional non-toxic pharmaceutically acceptable carriers, adjuvants or vehicles. The term "parenteral" or "parenterally" as used herein includes subcutaneous, intra-cutaneous, intra-venous, intra-muscular, intra-articular, intra-synovial, intra-sternal, intra-thecal, intra-lesional and intracranial injection or infusion techniques.

For intravenous administration, pharmaceutical compositions of the invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions.

Pharmaceutical compositions of the invention may be orally administered in any orally acceptable dosage form including, but not limited to, capsules, tablets, and aqueous suspension and solutions. In the case of tablets for oral and carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or coloring agents may be added.

Pharmaceutical compositions of the invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

It will be appreciated that the actual dosages of the agents of this invention will vary according to the particular agent being used, the particular composition formulated, the mode of administration, and the particular site, host, and disease being treated. Those skilled in the art using: conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals, preferably between 0.01 and about 25 mg/kg body weight per day, and more preferably between about 0.5 and about 25 mg/kg body weight per day of the active ingredient compound useful in the prevention and treatment of viral infection, including HIV infection.

Furthermore, the pharmaceutically acceptable formulations of the present invention may contain a compound of the present invention, or a pharmaceutically acceptable salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The pharmaceutical compositions of this invention may be administered as a continuous infusion, once per day, multiple times per day (e.g., from about 1 to about 5 times per day), once per week, twice per week, three times per week, every other day, every other week or as determined by the practicing clinician. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary or desired. Subsequently, the dosage or frequency of administration, or both, may be reduced, as a function of the symptoms, to a level at which the improved condition is retained or maintained. When the symptoms have been alleviated to the desired level, treatment should cease, at least in principle. Patients may, however, require intermittent treatment on a long-term basis, upon any recurrence of disease symptoms, especially for AIDS.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

With respect to the compounds of the present invention, the particular pharmaceutical formulation, the dosage, and the number of doses given per day to a mammal requiring such treatment, are all choices within the knowledge of one of ordinary skill in the art and can be determined without undue experimentation. For example, see "Guidelines for the Use of Antiretroviral Agents in HIV-1 Infected Adults and Adolescents," United States Department of Health and Human Services, available at http://aidsinfo.nih.gov/Guidelines/Default.aspx?MenuItem=Guidelines.

The compounds of this invention are also useful as commercial reagents which effectively bind to HIV integrase. As commercial reagent, the compounds of this invention, and their derivatives, may be used to block integration of a target DNA molecule by integrase, or may be derivatized to bind to a stable resin as a tethered substrate for affinity chromatography applications. These and other uses which characterize commercial integrase inhibitors will be evident to those of ordinary skill in the art.

The compounds of the present invention can be used alone (monotherapy) or administered in combination with one or more other HIV-inhibiting agents including but not limited to additional compounds of the invention or entry inhibitors, protease inhibitors, reverse transcriptase inhibitors, fusion inhibitors, and integrase inhibitors, examples of which are described below and known to the skilled artisan.

In one example, the compounds of the invention can be used in combination with an additional HIV integrase inhibitor. Compounds that effectively inhibit HIV integrase may provide improved antiviral agents and compositions for treating HIV infection (Wai, J. S. et al., J. Med. Chem. 43:4923-4926 (2000); Grobler, J. et al., PNAS 99: 6661-6666 (2002); Pals, G. C. G. et al., J. Med. Chem. 45: 3184-3194 (2002); Young, S. D., Curr. Opin. Drug Disc. & Devel. 4(4): 402-410 (2001); Godwin, C. G. et al., J. Med. Chem. 45: 3184-3194 (2002); Opar, A. Nature Reviews, Drug Discovery, vol. 6, p. 258-259, (2007)). Other integrase inhibitors known in the art include those disclosed in patent applications WO200510305, WO2004039803, WO2004067531, WO2008/048538, WO2003082881 WO 2007000043, and WO09146555.

The compounds of this invention may be administered in combination with antiviral agents which target other steps in the retroviral replication cycle. For example, the co-administered antiviral agent can be one that targets early events in the life cycle of the virus, such as cell entry, reverse transcription and viral DNA integration into cellular DNA. Antiviral agents targeting such early life cycle events include, didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4-bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformiate, eflornithine, ribavirin, acyclovir, alpha interferon and trimenotrexate. Additionally, non-ribonucleoside inhibitors of reverse transcriptase, such as TIBO, efavirenz, nevirapine or delavirdine, may be used to potentiate the effect of the compounds of this invention, as may viral uncoating inhibitors, inhibitors of trans-activating proteins such as tat or rev, or inhibitors of the viral protease. These compounds may also be co-administered with other inhibitors of HIV integrase.

Combination therapies according to this invention may exert an additive or combined inhibitory effect on HIV replication because each therapeutic agent of the combination acts on a different site of HIV replication or a synergistic effect. For example, the use of such combination therapies also advantageously enables a reduction in the dosage of each anti-retroviral agent, compared to administration of either agent alone as a monotherapy, while providing an equivalent or better therapeutic or prophylactic effect. Administration of lower doses of each therapeutic agent often reduces or even eliminates side effects or toxicity relative to monotherapy. Furthermore, combination therapies reduce the potential for the development of viral resistance to the agents administered compared to monotherapy.

Preferred combination therapies include the administration of a compound of this invention with AZT, 3TC, ddI, ddC, d4T, tenofovir, FTC, Combivir® (AZT/3TC combination), abacavir, efavirenz, nevirapine and delavirdine. The compounds of this invention may also be co-administered with other HIV protease inhibitors such as saquinavir, indinavir, nelfinavir, ritonavir, atazanavir, darunavir, and amprenavir. Combination of the compounds of this invention with such protease inhibitors may increase the therapeutic or prophylactic against various HIV viral mutants, HIV quasi species or other closely related viruses.

The compounds of this invention may be administered in combination with nucleoside or non-nucleoside retroviral reverse transcriptase inhibitors (e.g. derivatives of AZT or HIV aspartyl protease inhibitors) HIV-entry inhibitors, HIV integrase inhibitors, immuno-modulators (e.g., bropirimine, anti-human alpha interferon antibody, IL-2, GM-CSF, methionine enkephalin, interferon alpha, diethyldithiocarbante, tumor necrosis factor, naltrexone and rEPO); antibiotics (e.g., pentamidine isethionate), vaccines or a combination thereof.

Administration of the compounds of this invention in combination therapies with other agents to patients may be sequential or concurrent. Furthermore, pharmaceutical or prophylactic compositions of this invention may include a combination of an integrase inhibitor compound of the present invention and another therapeutic or prophylactic agent or HIV-inhibiting agent. Additional examples of agents useful for treating AIDS and HIV and suitable for combination therapies with the compounds of this invention are listed in Tables 1 and 2 below.

TABLE 1

| Antiviral Drug | Manufacturer | Indication |
| --- | --- | --- |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Waqrner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Darunavir (PI) | Tibotec/J&J | HIV infection, AIDS, ARC |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddCDideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| EL10 | Elan Corp, PLC (Gainesville, GA) | HIV infection |
| Emtricitabine (FTC) | Gilead | HIV infection, AIDS, ARC |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside RT inhibior) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |

TABLE 1-continued

| Antiviral Drug | Manufacturer | Indication |
|---|---|---|
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Noveferon Labs, Inc. (Akron, OH) | HIV inhibitor |
| Peptide T Octapeptide Sequence | Peninsula Labs (Belmont, CA) | AIDS |
| Trisodiumn Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Byrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribaflavin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, combination with AZT |
| Zitovudine; AZT | Glaxo Wellcome | HIV infection, AIDS, ARC, Kaposi's sarcoma, in combination with other therapies |
| Tenofovir disoproxil, fumarate salt (Viread ®) (RT inhibitor) | Gilead | HIV infection, AIDS |
| Combivir ® (RT inhibitor) | GSK | HIV infection, AIDS |
| abacavir succiate (or Ziagen ®) (RT inhibitor) | GSK | HIV infection, AIDS |
| Reyataz ® (atazanavir) | Bristol-Myers Squibb | HIV infection, AIDS |
| Fuzeon (Enfuvirtide, T-20) | Rocheh/Trimeris | HIV infection, AIDS, viral fusion inhibitor |
| Trizivir ® | GSK | HIV infection, AIDS |
| Kaletra ® | Abbott | HIV infection, AIDS, ARC |

TABLE 2

| Immuno-Modulator | Manufacturer | Indication |
|---|---|---|
| Acemannan | Carrington Labs Inc. (Irving, TX) | AIDS, ARC |
| Alpha-2 Interferon | Schering Plough | Kaposi's sarcoma w/AZT, AIDS |
| AS-101 Bropirimine | Wyeth-Ayerst/Pharmacia Upjohn | AIDS, advanced AIDS |
| CL246,738 | American Cyanamid Lederle Labs | AIDS, Kaposi's sarcoma |
| EL10 | Elan Corp PLC (Gainesville, GA) | HIV infection |
| FP-21399 | Fuki ImmunoPharm | Blocks HIV fusion with CD4+ cells ARC, in combination w/TNF (tumor necorsis factor) |
| Gamma Interferon | Genentech | |
| Granulocyte Macrophage Colony Stimulating Factor | Genetics Institute/Sandoz | AIDS |
| Granulocyte Macrophage Colony Stimulating Factor | Hoechst-Roussel\Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche/Immunex | AIDS, ARC, HIV, in combination w/AZT |
| IL-2 Interleukin-2 (aldeslukin) | Chiron | AIDS, increase in CD4 cell counts |
| IMERG-2 | Imreg (New Orleans, LA) | AIDS, Kaposi's sarcoma, ARC, PGL |
| Immune Globulin Intravenous | Cutter Biological (Berkeley, CA) | Pediatric AIDS, in combination w/AZT |

TABLE 2-continued

| Immuno-Modulator | Manufacturer | Indication |
| --- | --- | --- |
| IMREG-1 | Imreg (New Orleans, LA) | AIDS, Kaposi's sarcoma, ARC, PGL |
| Imuthiol Diethyl Dithio Carbamate | Merieux Institute | AIDS, ARC |
| Interferon Alfa 2a | Hoffman-La Roche | Kaposi's sarcoma, AIDS, in combination w/AZT ARC |
| Methionine-Enkephalin | TNI Pharmaceutical (Chicago, IL) | AIDS, ARC |
| MTP-PE Muramyl-Tripeptide Stimulating Factor | Ciba-Geigy Corp./Amgen | Kaposi's sarcoma AIDS in combination w/AZT |
| rCD4 Soluble Human CD4 rCD4-IgG | Genentech | AIDS, ARC Recombinant AIDS, ARC hybrids |
| Recombinant Soluble Human CD4 | Biogen | AIDS, ARC |
| Remune | Immune Response Corp. | Immunotherapeutic |

Anti-infectives that may be used in combination with the compounds of the present invention include, but are not limited to, atovaquone, azithromycin, clarithromycin, trimethoprim, trovafloxacin, pyrimethamine, daunorubicin, clindamycin with primaquine, fluconazole, pastill, ornidyl, eflornithine pentamidine, rifabutin, spiramycin, intraconazole-R51211, trimetrexate, daunorubicin, recombinant human erythropoietin, recombinant human growth hormone, megestrol acetate, testerone, and total enteral nutrition.

Antifungals that may be used in combination with the compounds of the present invention include, but are not limited to, anidulafungin, C31 G, caspofungin, DB-289, fluconzaole, itraconazole, ketoconazole, micafungin, posaconazole, and voriconazole.

Other compounds that may be used in combination with the compounds of the present invention include, but are not limited to, acmannan, ansamycin, LM 427, AR177, BMS-232623, BMS-234475, CI-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

Compounds of the present invention may be administered in combination with an additional agent or pharmaceutical composition that increases the bioavailability or slows the metabolism of the compounds. Agents or pharmaceutical compositions that may increase the bioavailability or slow the metabolism of the compounds herein include inhibitors of at least one isoform of the cytochrome P450 (CYP450) enzymes, preferably CYP1A2, CYP2d6, CYP2C9, CYP2C19 and CYP3A4. Suitable agents that may be used to inhibit CYP 3A4 include, but are not limited to, delavirdine and ritonavir. Such combinations may be administered such that a compound or compounds of the present invention are present in a single formulation or in the form of separate formulations that may be administered sequentially with an appropriate period of time in between or simultaneously. The choice of whether to include the compound or compounds of the present invention in the same formulation as the additional agent or agents is within the knowledge of one of ordinary skill in the art.

Preparation of Intermediates and Compounds

Four general approaches (synthetic schemes) were use to prepare the compounds of the present invention.

The first approach (Scheme 1) starts from pyridoxine which is modified to produce Intermediate aldehyde I using methodologies described in Paul et al. J. Med. Chem., 1977, 20 p 745. Reaction of this intermediate with aryl Grignard reagents leads to an intermediate alcohol II. Through a series of controlled oxidations, an intermediate keto-ester VII is obtained which can be selectively reduced to chiral alcohol-ester VIII using established chiral borane chemistry. The final compound IX is then formed by deprotection of the acetonide with formic acid followed by conversion of the ester to a hydroxamic acid with hydroxylamine.

The second approach (Scheme 2) consists of the deprotection and oxidation of the intermediate methyl 5-((4-methoxybenzyloxy)methyl)-2,2-dimethyl-4H-[1,3]dioxino[4,5-c]pyridine-8-carboxylate XII, as described in WO09146555, to produce the corresponding aldehyde-ester XIV. This intermediate is then reacted with Grignard reagents to give the (rac) alcohol ester VIII intermediate. Compound VII can then be converted to the final product IX, XI following the procedures described in Scheme 1.

The third approach (Scheme 3) starts from methyl 3-(benzyloxy)-5-formyl-4-methylpicolinate XV an intermediate obtained by the selective benzylation of methyl 3-(hydroxy)-5-formyl-4-methylpicolinate as described in WO09146555. Further reaction with an aryl Grignard reagent leads to an alcohol ester XVI. This alcohol XVI is acylated with acetic anhydride and reduced to the methylene XVIII through catalytic hydrogenation. Further transformation to the final compound XIX can be carried out using the methods described in Scheme 1.

The fourth (Scheme 4) approach begins with the alcohol-ester intermediate XVI obtained in Scheme 3. This alcohol is oxidized to the ketone XX and reacted with hydroxylamine. Deprotection followed by chromatography provided two compounds, the bis and mono addition products of hydroxylamine XXIII and XXII respectively.

Scheme 1
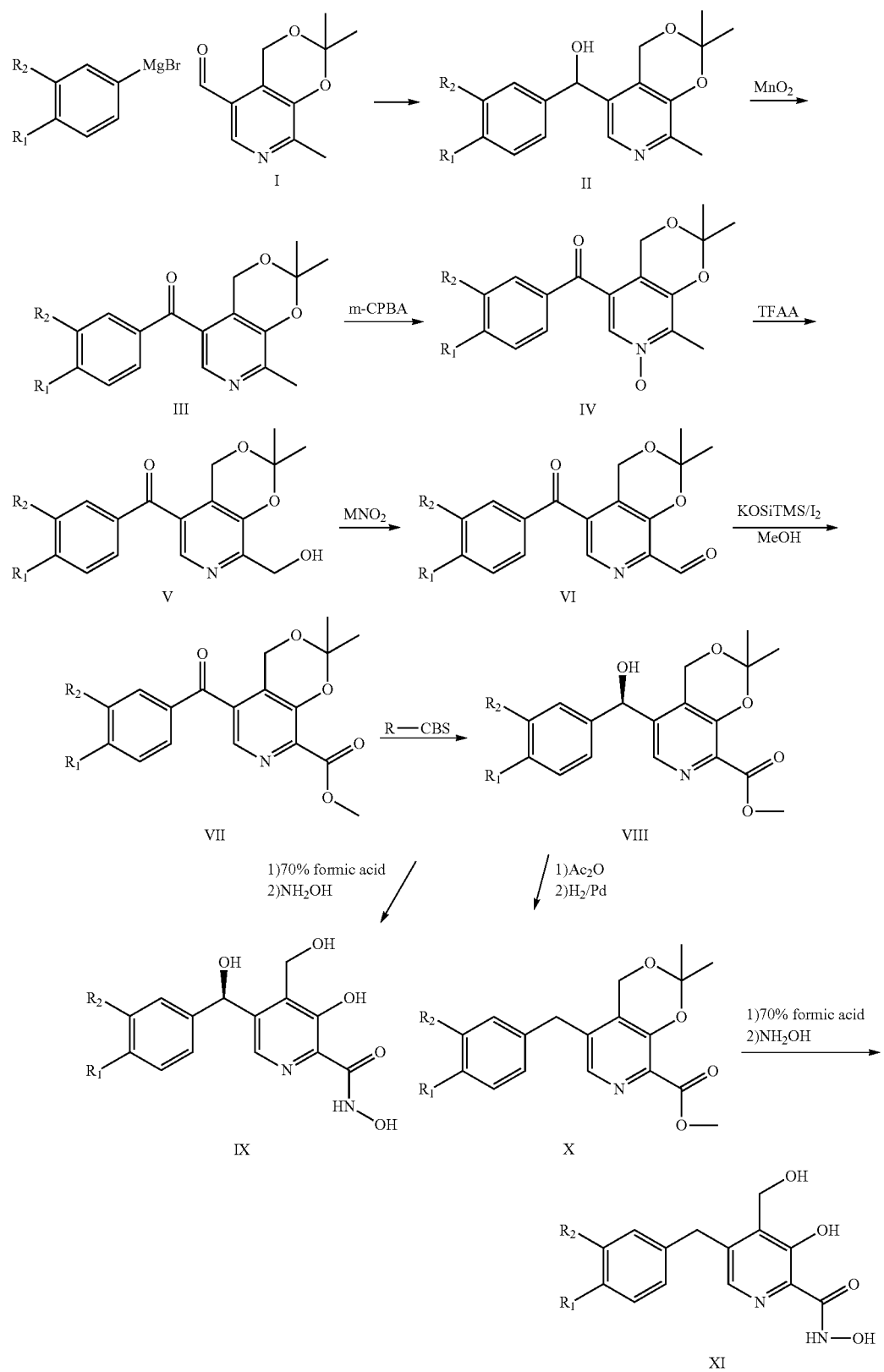

Scheme 2
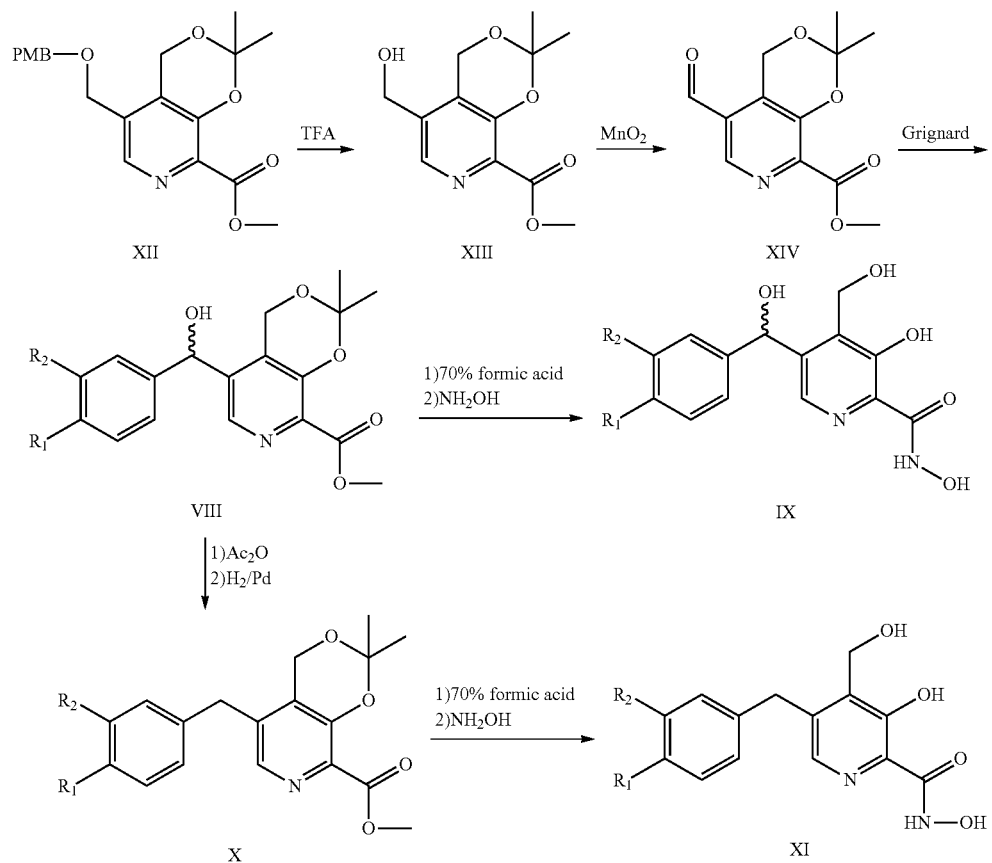
Scheme 3
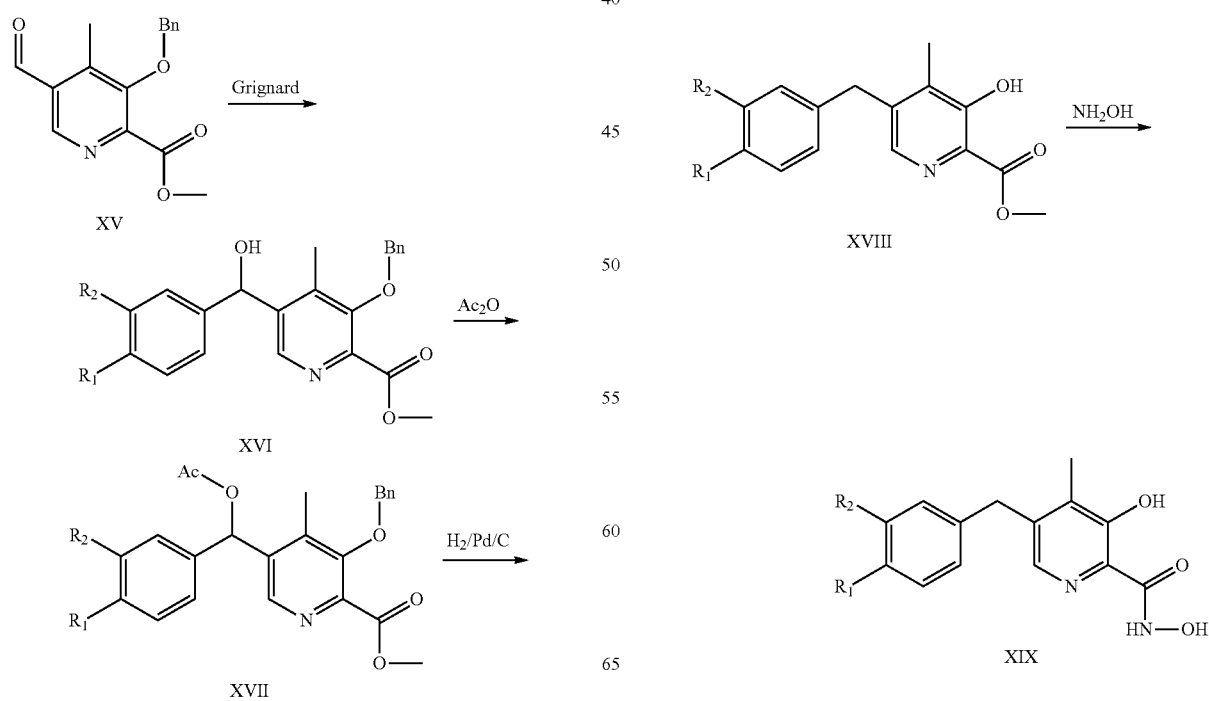

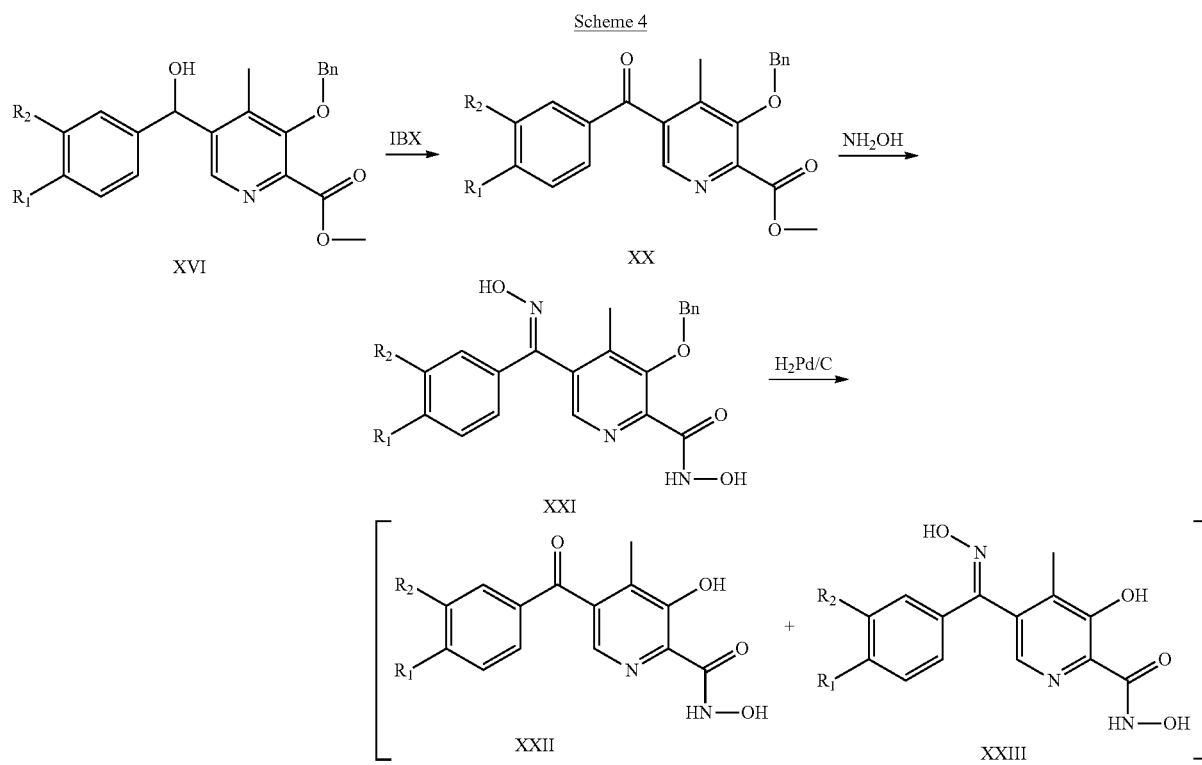

Scheme 4

General Procedures

Preparative chromatography was performed by flash chromatography, using silica gel 60 (EM Science) with the indicated solvent systems and positive air pressure, to allow for a proper rate of elution, or with a Biotage SP4™ automated chromatography system. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid, followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Unless otherwise indicated: all starting materials were purchased from a commercial source such as Aldrich Co. or Sigma Co; melting points (mp) were determined on a Büchi 530 melting point apparatus in capillary tubes (uncorrected); mass spectra were recorded on a Hewlett Packard LC/MSD 1100 system APCI either in negative mode or positive mode; nuclear magnetic resonance (NMR) spectra were recorded on a Bruker AMX 400 equipped with a reversed or QNP probe.

Samples were dissolved in deutero-chloroform ($CDCl_3$), deuterium oxide ($D_2O$) or deutero-dimethylsulfoxide (DMSO-$d_6$) for data acquisition and tetramethylsilane was used as internal standard. Chemical shifts (δ) are expressed in parts per million (ppm), coupling constants (J) are expressed in hertz (Hz) and multiplicities are denoted as s for singlet, d for doublet, dd for doublet of doublets, t for triplet, q for quartet, quint for quintet, m for multiplet, and br s for broad singlet.

EXAMPLES

Example 1

Preparation of (R)-5-((3-Chloro-4-fluorophenyl)(hydroxy)methyl)-N,3-dihydroxy-4-(hydroxymethyl)picolinamide Step 1a: preparation of (3-Chloro-4-fluorophenyl)(2,2,8-trimethyl-4H-[1,3]dioxino[4,5-c]pyridin-5-yl)methanol 1.2 g of 50 mmol magnesium turnings were washed, placed in a flame dried 3N RBF and 30 mL ether was added. 8.3 g of 40 mmol (1-Bromo-4-Fluoro-3-Chloro)-benzene was diluted in 20 mL ether and added drop wise to the Mg turnings under argon. The Grignard reaction was then initiated by heating briefly and was complete after ~2 h. 6.2 g of 30 mmol 2,8-dimethyl-4H-[1,3]dioxino[4,5-c]pyridine-5-carbaldehyde was diluted in 25 mL of ether and added drop wise at RT to the Grignard reagent.

A thick paste formed near the end of the addition of the Grignard reagent. After completion the mixture was sonicated briefly to break up clumps of the Mg salt. After 30 min the mixture was quenched by addition of aq. $NH_4Cl$, filtered to remove MgO and partitioned. The ether phase was collected and dried with $MgSO_4$ then evaporated yielding thick oil. The thick oil was then diluted with EtOAc whereupon the product crystallized and precipitated. 0.1 volume of hexane was added and the mixture cooled. Filtration gave a clean white product (6.4 g), and further standing of the concentrated liquor gave another 1.2 g (20.8 mmol) (70% yield).

Step 1b: preparation of (3-Chloro-4-fluorophenyl)(2, 2,8-trimethyl-4H-[1,3]dioxino[4,5-c]pyridin-5-yl) methanone 6.6 g of (4-fluorophenyl)(2,2,8-trimethyl-4H-[1,3]dioxino [4,5-c]pyridin-5-yl)methanol was dissolved with heat in 150 mL of CHCl$_3$. 12 g of MnO$_2$ was added to this solution and the suspension was refluxed for 2 h. The MnO$_2$ was then filtered over a 1 cm pad of silica gel and the clear organic phase evaporated to yield pure (3-Chloro-4-fluorophenyl) (2,2,8-trimethyl-4H-[1,3]dioxino[4,5-c]pyridin-5-yl)methanone.

Step 1c: preparation of 5-(3-Chloro-4-fluorobenzoyl)-2,2,8-trimethyl-4H-[1,3]dioxino[4,5-c]pyridine 7-oxide 6.2 g of (3-Chloro-4-fluorophenyl)(2,2,8-trimethyl-4H-[1, 3]dioxino[4,5-c]pyridin-5-yl)methanone (1b) was dissolved in 130 mL CHCl$_3$ and 6 g of 70% meta-Chloroperoxybenzoic acid (mCPBA) was added in one portion. The reaction mixture was stirred for 25 min to the completion of the reaction. 100 mL of 1M K$_2$CO$_3$ was added and the organic phase extracted. The remaining aqueous phase was extracted with two 50 mL portions of CHCl$_3$ and the organic phases were combined. 25 g of CaCO$_3$ was added to the organic phase and stirred for 15 min. Filtration of the CaCO$_3$ gave a light yellow solution of clean product. Evaporation afforded 6.2 g of the desired product (1c).

Step 1d: Preparation of (3-Chloro-4-fluorophenyl)(8-(hydroxymethyl)-2,2-dimethyl-4H-[1,3]dioxino[4, 5-c]pyridin-5-yl)methanone 5.5 g of 5-(4-fluorobenzoyl)-2,2,8-trimethyl-4H-[1,3]dioxino[4,5-c]pyridine 7-oxide was dissolved in 20 mL dichloromethane (DCM) in 5 mL of Trifluoroacetic anhydride (TFAA) followed by vigorous boiling. When the boiling subsided an additional 30 mL of TFAA was added and the solution was stirred overnight (14 h). TLC revealed completion of the reaction (R$_f$ EtOAc; (s.m. 0.2), product 0.9). The DCM was removed by evaporation and the solvent switched to MeOH (100 mL). This solution was stirred for 30 min after which evaporation affording thick oil. Toluene was added and removed under high vacuum yielding a foam containing the desired product (1d).

Step 1e: Preparation of 5-(3-Chloro-4-fluorobenzoyl)-2,2-dimethyl-4H-[1,3]dioxino[4, 5-c]pyridine-8-carbaldehyde (4-fluorophenyl)(8-(hydroxymethyl)-2,2-dimethyl-4H-[1,3]dioxino[4,5-c]pyridin-5-yl)methanone (total yield from step 1d) was added to 200 mL of CHCl$_3$ and 15 g MnO$_2$. The resulting suspension was refluxed for 4 h to completion. MnO$_2$ was then removed by filtration through Celite and washed 2× with CHCl$_3$. Evaporation of the solvent gave 5 g of crude product which was used without further purification.

Step 1f: preparation of methyl 5-(3-Chloro-4-fluorobenzoyl)-2,2-dimethyl-4H-[1, 3]dioxino[4, 5-c]pyridine-8-carboxylate 4.0 g (11.5 mmol) of crude 5-(4-fluorobenzoyl)-2,2-dimethyl-4H-[1,3]dioxino[4,5-c]pyridine-8-carbaldehyde was added to a solution of 4 g potassium trimethylsilanoate in 150 mL MeOH, followed by 4 g of I$_2$ powder. This mixture was stirred for 1 h at RT. The methanol was then removed and replaced by EtOAc which was then extracted vs. saturated NaHCO$_3$ containing metabisulfite (5% 1 vol). The organic phase was dried and evaporated, residual oil was dissolved in hot hexane and activated charcoal was added. This mixture was filtered hot yielding a concentrated light yellow solution that was allowed to cool to 4° C. whereupon a solid separated. 4.0 g of this solid was then filtered, dried and dissolved in hot TBME (also with a few drops of DCM to clarify). This solution was then cooled at −10° C. for 1 h. An off-white solid was filtered off and dried overnight to yield 2.6 g (60% yield) of desired product (10. The supernatant was allowed to evaporate giving a sticky solid containing the desired crude product.

Step 1g: Preparation of (R)-methyl 5-((3-Chloro-4-fluorophenyl)(hydroxy)methyl)-2,2-dimethyl-4H-[1, 3]dioxino[4,5-c]pyridine-8-carboxylate 100 mg of R-methyl (CBS) was dissolved in 10 mL THF. 3 mL 1.0 M borane THF was then added and the mixture cooled to −20° C. with an argon atmosphere. 1 g of the ketone was dissolved in 10 mL THF and added drop wise over 1.5 h with the temperature slowly warming to RT. stirring was left for 2 h. 10 mL of anhydrous MeOH was then added and the mixture heated to −50° C. to quench the reaction (H$_2$ evolution). The solvent was evaporated and replaced with anhydrous MeOH, stirred for 30 min and once again evaporated.

Step 1h: preparation of (R)-5-((3-Chloro-4-fluorophenyl)(hydroxy)methyl)-N,3-dihydroxy-4-(hydroxymethyl)picolinamide The crude product from step 1g, (R)-methyl 5-((3-Chloro-4-fluorophenyl)(hydroxy)methyl)-2,2-dimethyl-4H-[1,3]dioxino[4,5-c]pyridine-8-carboxylate, was dissolved in 4 mL of pyridine and 1.5 mL of 50% hydroxylamine in water producing a clear yellow solution that was then heated to 80° C. for 1 h (complete conversion). The aqueous pyridine was then evacuated by vacuum distillation and the residual oil dissolved in EtAc. Extraction with 10% citric acid removed residual pyridine and hydroxylamine. The organic phase became cloudy as deprotection of the acetonide was initiated. The EtAc was removed and the residual oil dissolved in 3 mL 70% formic acid. This solution was left to rest at RT for 30 min upon which completion of the deprotection was noted. The oil was then diluted with 20 mL of water and 70 mL of EtAc and the product was extracted into the organic phase. A black aqueous layer formed and was extracted with one 50 mL portion of EtAc. Following this extraction the organic phase was concentrated (to 20 mL) and extracted with 0.1N NaOH (2×20 mL). The aqueous layer was then removed and washed with hexane. The aqueous layer was again removed and acidified until complete precipitation of the product (acid pH) was observed. The precipitate was then extracted into EtAc and the aqueous layer back extracted. Evaporation of the solvent gave a foam product. MeCN (1 mL) was added to dissolve followed by hexane producing a biphasic mixture. Stirring for 30 min gave a crystalline powder precipitate which was filtered off yielding 0.56 g off-white powder.

$^1$H-NMR (400 MHz, dmso): δ=13.01 (s, 1H), 12.0 (s, 1H), 9.51 (s 1H), 9.02 (t 1H), 8.11 (s, 1H), 7.60 (d 1H), 7.40 (m, 2H), 5.1 (s, 1H), 4.48 (s, 2H); MS-ESI m/z 343 [MH]$^+$.

Example 2

Preparation of 5-(4-fluorobenzyl)-N,3-dihydroxy-4-(hydroxymethyl)picolinamide

Step 2a: preparation of methyl 5-((4-fluorophenyl)(hydroxy)methyl)-2,2-dimethyl-4H-[1,3]dioxino[4,5-c]pyridine-8-carboxylate A 4-fluorophenyl magnesium bromide solution (0.438 mL of 1M in tetrahydrofuran, 30.0 mmol, 1.1 eq) at −78° C. was added to a methyl 5-formyl-2,2-dimethyl-4H-[1,3]dioxino[4,5-c]pyridine-8-carboxylate solution (0.100 g, 0.398 mmol, 1 eq. in 5.0 mL of tetrahydrofurane). The reaction mixture was stirred for 20 min. at −78° C. A saturated bicarbonate solution was added and reaction mixture was extracted with ethyl acetate. The organic phases were combined, dried over magnesium sulphate and concentrated under reduced pressure yielding 0.065 g of crude product methyl 5-((4-fluorophenyl)(hydroxy)methyl)-2,2-dimethyl-4H-[1,3]dioxino[4,5-c]pyridine-8-carboxylate 2a (47% yield) as a white solid.

$^1$H-NMR. MS-ESI m/z 348 [MH]$^+$.

Step 2b: preparation of methyl 5-((4-fluorophenyl)(acetoxy)methyl)-2,2-dimethyl-4H-[1,3]dioxino[4,5-c]pyridine-8-carboxylate Trietylamine (0.031 g, 0.300 mmol, 3 eq) and acetic anhydride (0.011 g, 0.111 mmol, 1.1 eq) were added to a solution of methyl 5-((4-fluorophenyl)(hydroxy)methyl)-2,2-dimethyl-4H-[1,3]dioxino[4,5-c]pyridine-8-carboxylate 2a in 4.0 mL of dichloromethane. This reaction mixture was stirred for 1 hour at room temperature followed by addition of a saturated bicarbonate solution. The reaction mixture was then extracted with ethyl acetate and the organic phases were combined and concentrated under reduced pressure yielding 0.039 g of crude product 2b (100% yield) as a white solid.

$^1$H-NMR. MS-ESI m/z 390 [MH]$^+$.

Step 2c: preparation of methyl 5-(4-fluorobenzyl)-2,2-dimethyl-4H-[1,3]dioxino[4,5-c]pyridine-8-carboxylate 0.039 g of Methyl 5-((4-fluorophenyl)(acetoxy)methyl)-2,2-dimethyl-4H-[1,3]dioxino[4,5-c]pyridine-8-carboxylate (0.100 mmol, 1 eq) and 5 mg of 10% Pd/C were added to 4.0 mL of methanol and stirred under atmospheric hydrogen overnight. The catalyst was filtered and the crude product was purified by silica gel (40% ethyl acetate/hexane) yielding 0.016 g of the desired product 2c (50% yield) as a white solid.

MS-ESI m/z 332 [MH]$^+$.

Step 2d: preparation of 5-(4-fluorobenzyl)-N,3-dihydroxy-4-(hydroxymethyl)picolinamide 5.0 mL of a hydroxylamine solution (50 wt. % in water) was added to a solution of 0.015 g of methyl 5-(4-fluorobenzyl)-2,2-dimethyl-4H-[1,3]dioxino[4,5-c]pyridine-8-carboxylate (0.045 mmol, 1 eq) in 5.0 mL of tetrahydrofuran. This reaction mixture was stirred at reflux 6 hrs. The pH was adjusted to 6 and reaction mixture was extracted with ethyl acetate. Organic phases were combined, dried over magnesium sulphate and concentrated under vacuum to give 0.006 g of the desired product (2d) (40% yield) as a white solid.

$^1$H-NMR (400 MHz, MeOD): δ=8.17 (s, 1H), 7.44 (m, 2H), 7.09 (t, 2H), 4.78 (s, 2H), 4.58 (s, 2H); MS-ESI m/z 293 [MH]$^+$.

Example 3

Preparation of 5-((4-fluorophenyl)(hydroxy)methyl)-N,3-dihydroxy-4-(hydroxymethyl)picolinamide Hydroxylamine 50% in 3.0 mL of water was added to methyl 5-((4-fluorophenyl)(hydroxy)methyl)-2,2-dimethyl-4H-[1,3]dioxino[4,5-c]pyridine-8-carboxylate 2a (0.030 g, 0.086 mmol, 1 eq) in 5.0 mL of tetrahydrofuran. The reaction mixture was stirred at reflux overnight. The pH was adjusted to 6 and reaction mixture was extracted with ethyl acetate. The resulting organic phases were combined, dried over magnesium sulphate and concentrated under vacuum. The crude product was purified by Biotage reverse phase chromatography yielding 0.015 g of 3 (58% yield) as a white solid. δ=8.19 (s, 1H), 7.46 (m, 2H), 7.09 (t, 2H), 5.08 (s, 1H), 4.58 (s, 2H); MS-ESI m/z 309 [MH]$^+$.

Example 4

Preparation of 5-((4-fluorophenyl)(hydroxy)methyl)-N-hydroxy-N,2,2-trimethyl-4H-[1,3]dioxino[4,5-c]pyridine-8-carboxamide 1.8 mL of lithium bis(trimethylsilyl)amide solution (1.809 mmol, 9 eq, 1M in tetrahydrofuran) was added to 0.041 g of N-methylhydroxylamine hydrochloride (0.249 mmol, 1.1 eq.) in 5.0 mL of tetrahydrofuran (−78° C.) and stirred for 10 min at 78° C.

0.070 g of methyl 5-((4-fluorophenyl)(hydroxy)methyl)-2,2-dimethyl-4H-[1,3]dioxino[4,5-c]pyridine-8-carboxylate solution (0.201 mmol, 1 eq.) in 3.0 mL of tetrahydrofuran was then added followed by stirring for 30 min at −78° C. Water was then added to the reaction mixture followed by extraction with ethyl acetate. The resulting organic phases were then combined and concentrated under reduced pressure yielding 0.01 g of crude product (14% yield) as a white solid.

MS-ESI m/z 363 [MH]$^+$.

Example 5

Preparation of 5-((4-fluorophenyl)(hydroxy)methyl)-N,3-dihydroxy-4-(hydroxymethyl)-N-methylpicolinamide 2.0 mL of formic acid was added to 5-((4-fluorophenyl)(hydroxy)methyl)-N-hydroxy-N,2,2-trimethyl-4H-[1,3]dioxino[4,5-c]pyridine-8-carboxamide (0.010 g, 0.028 mmol, 1 eq). This reaction mixture was stirred at room temperature for 10 min. The formic acid was then concentrated under vacuum yielding 0.005 g of the desired product (5) (56% yield) as a yellow oil.

MS-ESI m/z 323 [MH]$^+$.

Example 6

Preparation of 5-((4-fluorophenyl)(hydroxy)methyl)-3-hydroxy-4-(hydroxymethyl)-N-methoxypicolinamide

Step 6a: preparation of 5-((4-fluorophenyl)(hydroxy)methyl)-N-methoxy-2,2-dimethyl-4H-[1,3]dioxino[4,5-c]pyridine-8-carboxamide Lithium bis(trimethylsilyl)amide (2.25 mL of a 1 M solution in tetrahydrofuran, 2.25 mmol, 6 eq. at −78° C.) was added to 0.034 g of methoxylamine hydrochloride (0.413 mmol, 1.1 eq) in 5.0 mL of tetrahydrofuran. This reaction mixture was stirred for 10 min. and a solution of 0.130 g methyl 5-((4-fluorophenyl)(hydroxy)methyl)-2,2-dimethyl-4H-[1,3]dioxino[4,5-c]pyridine-8-carboxylate (0.375 mmol, 1 eq) in 5.0 mL of tetrahydrofuran was added. The reaction mixture was stirred for 30 min at −78° C. and a saturated ammonium chloride solution was added. The reaction mixture was then extracted with ethyl acetate and the resulting organic phases were combined and concentrated under reduced pressure yielding 0.136 g of crude product 6a (100% yield) as a white solid.

MS-ESI m/z 390 [MH]$^+$.

Step 6b: preparation of 5-((4-fluorophenyl)(hydroxy)methyl)-3-hydroxy-4-(hydroxymethyl)-N-methoxypicolinamide 2.0 mL of formic acid was added to 0.136 g of the product of step 6a (0.376 mmol, 1 eq) and stirred at room temperature 1 hr. The formic acid was then concentrated under vacuum yielding 0.105 g of a yellow oil containing the desired product 6 (88%).

MS-ESI m/z 323 [MH]$^+$.

Example 7

Preparation of 5-(4-fluorobenzyl)-N,3-dihydroxy-4-methylpicolinamide

Step 7a: preparation of methyl 3-(benzyloxy)-5-((4-fluorophenyl)(hydroxy)methyl)-4-methylpicolinate 1.0 g of methyl 3-(benzyloxy)-5-formyl-4-methylpicolinate (3.50 mmol, 1 eq) was dissolved in 20.0 mL of tetrahydrofuran and 4.2 mL of a 4-fluorophenyl magnesium bromide solution (1M in tetrahydrofuran, 4.20 mmol, 1.2 eq) was added at −78° C. over a period of 1 hr. The reaction mixture was then stirred for 20 min. −78° C. A saturated bicarbonate solution was added and reaction mixture was extracted with ethyl acetate.

The resulting organic phases were combined, dried over magnesium sulphate and concentrated under reduced pressure. The crude product was purified by silica gel (50% ethyl acetate/hexane) yielding 0.70 g of colourless oil containing the desired product 7a (53% yield).

MS-ESI m/z 382 [MH]$^+$.

Step 7b: preparation of methyl 5-(acetoxy(4-fluorophenyl)methyl)-3-(benzyloxy)-4-methylpicolinate 0.70 g of 5-(4-fluorobenzyl)-N,3-dihydroxy-4-methylpicolinamide was dissolved in 10.0 ml of dichloromethane and 0.281 g of triethylamine (2.78 mmol, 5 eq.), 2.0 mg of DMAP and 0.170 g of acetic anhydride (1.669 mmol, 3 eq.) were added to the solution.

This reaction mixture was stirred 1 hour at room temperature and a saturated solution of bicarbonate was added. The reaction mixture was extracted with ethyl acetate and organic phases were combined and concentrated under reduced pressure yielding 0.260 g of crude product, 7b, (93% yield) as a white solid.

MS-ESI m/z 424 [MH]$^+$.

Step 7c: preparation of methyl 5-(4-fluorobenzyl)-3-hydroxy-4-methylpicolinate

The product of step 7b (0.260 g, 0.615 mmol, 1 eq) and 10% Pd/C (20 mg) in methanol (4.0 mL) were stirred under an atmospheric hydrogen overnight. The catalyst was then filtered and the crude product was purified by silica gel (40% ethyl acetate/hexane) to give 0.169 g of 7c (100%) as a white solid.

MS-ESI m/z 276 [MH]$^+$.

Step 7d: preparation of 5-(4-fluorobenzyl)-N,3-dihydroxy-4-methylpicolinamide 5.0 mL of hydroxylamine solution (50 wt. % in water) was added to a solution of 0.169 g of methyl 5-(4-fluorobenzyl)-3-hydroxy-4-methylpicolinate 7c (0.615 mmol, 1 eq) in 5.0 mL of tetrahydrofuran. The reaction mixture was stirred at reflux overnight.

The pH was adjusted to 6 and reaction mixture was extracted with ethyl acetate. The organic phases were combined, dried over magnesium sulphate and concentrated under vacuum. The crude product was purified by Biotage reverse phase chromatography yielding 0.120 g of the desired product 7 (71% yield) as a white solid.

MS-ESI m/z 277 [MH]$^+$.

Example 8

Preparation of 5-((4-fluorophenyl)(hydroxy)methyl)-N,3-dihydroxy-4-methylpicolinamide Step 8a: preparation of 3-(benzyloxy)-5-((4-fluorophenyl)(hydroxy)methyl)-N-hydroxy-4-methylpicolinamide 5.0 mL of a hydroxylamine solution (50 wt. % in water) was added to a solution of 0.239 g of methyl 3-(benzyloxy)-5-((4-fluorophenyl)(hydroxy)methyl)-4-methylpicolinate (0.627 mmol, 1 eq.; product of step 7a, example 7) in 5.0 mL of tetrahydrofuran. The reaction mixture was stirred at reflux overnight followed by extraction with ethyl acetate. The resulting organic phases were combined, dried over magnesium sulphate and concentrated under vacuum yielding 0.200 g of the desired product 8a (84% yield) as a white solid.

MS-ESI m/z 383 [MH]$^+$.

Step 8b: preparation of 5-((4-fluorophenyl)(hydroxy)methyl)-N,3-dihydroxy-4-methylpicolinamide 3-(benzyl oxy)-5-((4-fluorophenyl)(hydroxy)methyl)-N-hydroxy-4-methylpicolinamide (0.110 g, 0.288 mmol, 1 eq) and 10% Pd/C (5 mg) were dissolved in 4.0 mL of methanol and stirred under atmospheric hydrogen for 1 hour. The catalyst was then filtered and reaction mixture was concentrated under vacuum. The crude product was purified by Biotage reverse phase chromatography yielding 0.055 g of the desired product 8 (65% yield) as a white solid.

MS-ESI m/z 293 [MH]$^+$.

Example 9

Preparation of 5-(4-fluorobenzoyl)-N,3-dihydroxy-4-methylpicolinamide

Step 9a: preparation of methyl 3-(benzyloxy)-5-(4-fluorobenzoyl)-4-methylpicolinate 2-iodoxybenzoic acid (0.577 g, 2.06 mmol, 3 eq.) was added to a solution of 0.239 g of methyl 3-(benzyloxy)-5-((4-fluorophenyl)(hydroxy)methyl)-4-methylpicolinate (product of step 7a, example 7) in 250 mL of ethyl acetate (0.627 mmol, 1 eq.) and stirred at reflux for 1 hr. The solid was then filtered and the solution concentrated. The crude product was purified by silica gel (10% ethyl acetate/hexane) yielding 0.222 g of the desired product 9a (85% yield) as a white solid.

MS-ESI m/z 380 [MH]$^+$.

Step 9b: preparation of 3-(benzyloxy)-5-(4-fluorobenzoyl)-N-hydroxy-4-methylpicolinamide 5.0 mL of hydroxylamine solution (50 wt. % in water) was added to a solution of 0.222 g of methyl 3-(benzyloxy)-5-(4-fluorobenzoyl)-4-methylpicolinate (9a) in 5.0 mL of tetrahydrofuran (0.586 mmol, 1 eq). The reaction mixture was stirred at reflux overnight followed by extraction with ethyl acetate. The resulting organic phases were combined, dried over magnesium sulphate and concentrated under vacuum yielding 0.200 g of the desired product 9b (89% yield) as a white solid. MS-ESI m/z 430 [MH]$^+$.

Example 10

Preparation of (E)-5-((4-fluorophenyl)(hydroxyimino)methyl)-N,3-dihydroxy-4-methylpicolinamide 0.090 g of 3-(benzyloxy)-5-(4-fluorobenzoyl)-N-hydroxy-4-methylpicolinamide (9b; 0.237 mmol, 1 eq.) and 5 mg of 10% Pd/C were dissolved in 4.0 mL of methanol and stirred under an atmospheric hydrogen for 1 hr. The catalyst was then filtered and reaction mixture was concentrated under vacuum. The crude product was purified by Biotage reverse phase chromatography yielding 0.015 g of 5-(4-fluorobenzoyl)-N,3-dihydroxy-4-methylpicolinamide (the product step 9b, example 9) (22% yield) and 0.015 g of the corresponding oxime (E)-5-((4-fluorophenyl)(hydroxyimino)methyl)-N,3-dihydroxy-4-methylpicolinamide (10) (22% yield), both as a white solid.

MS-ESI m/z 291 [MH]$^+$

MS-ESI m/z 306 [MH]$^+$

Example 11

Preparation of (S)-5-((3-Chloro-4-fluorophenyl)(hydroxy)methyl)-N,3-dihydroxy-4-(hydroxymethyl)picolinamide The procedure described in Example 1 was followed using (S)-CBS as a chiral reducing agent in step 1 g.

TABLE 3

Listing of Compounds in Examples

| | Compound Name |
|---|---|
| Example 1 | (R)-5-((3-Chloro-4-fluorophenyl)(hydroxy)methyl)-N,3-dihydroxy-4-(hydroxymethyl)picolinamide |
| step 1a | (3-Chloro-4-fluorophenyl)(2,2,8-trimethyl-4H-[1,3]dioxino[4,5-c]pyridin-5-yl)methanol |
| step 1b | (3-Chloro-4-fluorophenyl)(2,2,8-trimethyl-4H-[1,3]dioxino[4,5-c]pyridin-5-yl)methanone |
| step 1c | 5-(3-Chloro-4-fluorobenzoyl)-2,2,8-trimethyl-4H-[1,3]dioxino[4,5-c]pyridine 7-oxide |
| step 1d | (3-Chloro-4-fluorophenyl)(8-(hydroxymethyl)-2,2-dimethyl-4H-[1,3]dioxino[4,5-c]pyridin-5-yl)methanone |
| step 1e | Step e 5-(3-Chloro-4-fluorobenzoyl)-2,2-dimethyl-4H-[1,3]dioxino[4,5-c]pyridine-8-carbaldehyde |
| step 1f | methyl 5-(3-Chloro-4-fluorobenzoyl)-2,2-dimethyl-4H-[1,3]dioxino[4,5-c]pyridine-8-carboxylate |
| step 1g | (R)-methyl 5-((3-Chloro-4-fluorophenyl)(hydroxy)methyl)-2,2-dimethyl-4H-[1,3]dioxino[4,5-c]pyridine-8-carboxylate |
| step 1h | (R)-5-((3-Chloro-4-fluorophenyl)(hydroxy)methyl)-N,3-dihydroxy-4-(hydroxymethyl)picolinamide |
| Example 2 | 5-(4-fluorobenzyl)-N,3-dihydroxy-4-(hydroxymethyl)picolinamide |
| step 2a | methyl 5-((4-fluorophenyl)(hydroxy)methyl)-2,2-dimethyl-4H-[1,3]dioxino[4,5-c]pyridine-8-carboxylate |
| step 2b | methyl 5-((4-fluorophenyl)(acetoxy)methyl)-2,2-dimethyl-4H-[1,3]dioxino[4,5-c]pyridine-8-carboxylate |
| step 2c | methyl 5-(4-fluorobenzyl)-2,2-dimethyl-4H-[1,3]dioxino[4,5-c]pyridine-8-carboxylate |
| step 2d | 5-(4-fluorobenzyl)-N,3-dihydroxy-4-(hydroxymethyl)picolinamide |
| Example 3 | 5-((4-fluorophenyl)(hydroxy)methyl)-N,3-dihydroxy-4-(hydroxymethyl)picolinamide |
| Example 4 | 5-((4-fluorophenyl)(hydroxy)methyl)-N-hydroxy-N,2,2-trimethyl-4H-[1,3]dioxino[4,5-c]pyridine-8-carboxamide |
| Example 5 | 5-((4-fluorophenyl)(hydroxy)methyl)-N,3-dihydroxy-4-(hydroxymethyl)-N-methylpicolinamide |
| Example 6 | 5-((4-fluorophenyl)(hydroxy)methyl)-3-hydroxy-4-)hydroxymethyl)-N-methoxypicolinamide |
| step 6a | -((4-fluorophenyl)(hydroxy)methyl)-N-methoxy-2,2-dimethyl-4H-[1,3]dioxino[4,5-c]pyridine-8-carboxamide |
| step 6b | 5-((4-fluorophenyl)(hydroxy)methyl)-3-hydroxy-4-(hydroxymethyl)-N-methoxypicolinamide |
| Example 7 | -(4-fluorobenzoyl)-N,3-dihydroxy-4-methylpicolinamide |
| step 7a | methyl 3-(benzyloxy)-5-((4-fluorophenyl)(hydroxy)methyl)-4-methylpicolinamide |
| step 7b | methyl 5-(acetoxy(4-fluorophenyl)methyl)-3-(benzyloxy)-4-methylpicolinate |
| step 7c | methyl 5-(4-fluorobenzyl)-3-hydroxy-4-methylpicolinate |
| step 7d | 5-(4-fluorobenzyl)-N,3-dihydroxy-4-methylpicolinamide |

TABLE 3-continued

Listing of Compounds in Examples

| | Compound Name |
|---|---|
| Example 8 | -((4-fluorophenyl)(hydroxy)methyl)-N,3-dihydroxy-4-methylpicolinamide |
| step 8a | 3-(benzyloxy)-5-((4-fluorophenyl)(hydroxy)methyl)-N-hydroxy-4-methylpicolinamide |
| Step 8b | 5-((4-fluorophenyl)(hydroxy)methyl)-N,3-dihydroxy-4-methylpicolinamide |
| Example 9 | -(4-fluorobenzoyl)-N,3-dihydroxy-4-methylpicolinamide |
| Step 9a | methyl 3-(benzyloxy)-5-(4-fluorobenzoyl)-4-methylpicolinate |
| Step 9b | 3-(benzyloxy)-5-(4-fluorobenzoyl)-N-hydroxy-4-methylpicolinamide |
| Example 10 | (E)-5-((4-fluorophenyl)(hydroxyimino)methyl)-N,3-dihydroxy-4-methylpicolinamide |
| Example 11, | (S)-5-((3-Chloro-4-fluorophenyl)(hydroxy)methyl)-N,3-dihydroxy-4-(hydroxymethyl)picolinamide |

Example 12

Biological Evaluation, In Vitro Integrase Inhibition Assay $IC_{50}$ was determined for the compounds of the inventions based on data generated in strand transfer assays. The $IC_{50}$ is a measure of the ability of the compounds tested to inhibit the integration of 3'-processed oligonucleotides by recombinant HIV-1 integrase.

Strand transfer assays were performed essentially as described in Hazuda, D. J.; Felock, P.; Hastings, J. C.; Pramanik, B.; Wolfe, A. J. Virol. 1997, 71, 7005-7011). Donor DNA (1.5 pmol/well), biotinylated on the 5' end of the strand processed by integrase, was immobilized onto streptavidin-coated microtiter plates. Recombinant integrase (250 ng/well) was assembled onto the immobilized donor oligonucleotide in reaction buffer (20 mM Hepes, pH 7.6, 5 mM B-mercaptoethanol, 50 ug/mL bovine serum albumin) containing 30 mM $MnCl_2$. Excess enzyme was removed, and the complexes were washed extensively prior to the addition of the target DNA substrate. The target DNA (0.75 pmoles/well) substrate was labeled on each 3' end with FITC. After strand transfer, the FITC-labeled products were detected using an anti-FITC antibody conjugated with alkaline phosphatase (Roche) and a chemi-luminescent substrate (Tropix CSPD with Sapphire II enhancer, Applied Biosystems). The assay was performed in a final concentration of 10% DMSO. To specifically evaluate inhibition of strand transfer, compounds were added after assembly, just prior to the addition of the target DNA.

The results of the integrase strand transfer assay are reported as $IC_{50}$ values. $IC_{50}$ values were determined using a sigmoidal dose-response equation. The formula used for calculating % inhibition was: % Inhibition=[1-(sample counts/average of positive control)]*100. The percent inhibition of HIV-1 integrase activity was graphed against the log of the compound concentration (M). Using GraphPad Prism or ActivityBase (IDBS) software $IC_{50}$ was determined using following sigmoidal dose-response equation:

$$Y=(A+((B-A)/(1+((C/X)^D))))$$

Where A is the lower plateau (~0%), B is the higher plateau (~100%), C is the $IC_{50}$, D is the slope, X is the compound concentration (M), and Y is the % inhibition.

Inhibition of strand transfer, as determined by their $IC_{50}$, demonstrates that the compounds of the present invention inhibit HIV integrase and have $IC_{50}$s similar to that of Raltegravir, a marketed HIV integrase inhibitor, and L-708906, an integrase inhibitor currently in clinical development (Table 4).

TABLE 4

Strand Transfer Assay $IC_{50}$ Data

| Compound | ST $IC_{50}$ |
|---|---|
| Raltegravir (MK-0518) | 0.065 |
| L-708906 (Merck) | 0.045 |
| Compound of Example 1 | 0.056 |
| Compound of Example 2 | 0.035 |
| Compound of Example 11 | 0.023 |

Example 13

Antiviral Efficacy

The antiviral efficacies of the integrase inhibitor compounds of the invention were evaluated based on $EC_{50}$ measures obtained from two different in vitro HIV infection assay using cultured MT-4 cells: (1) a multi-cycle infection where cells were infected with wild type NL-4.3) and (2) a single-cycle infection where the cells were infected with a luciferase-bearing, envelope defective (env-) NL-4.3 virus pseudotyped with HIV-1 env (HXBc2.

The incubation period for the multi-cycle infection assay was 6 days. Cell viability (cytoprotection) and $EC_{50}$ were determined using the colorimetric MTT assay (A. J. Japour et al, Antimicrobial Agents and Chemotherapy, 37, 1095-1101, 1993 and R. Pauwels et al. Journal of Virological Methods, 20, 309-321, 1988).

The incubation period for the single-cycle infection assay was 48 hours. $EC_{50}$ was determined, as described by Chen et al., Journal of Virology, February 1994, Vol. 68, No. 2, p. 654-660, based on measures of luciferase signal over a range of drug concentrations.

The results of these assays are shown in Table 5 and integrase inhibitors of the invention were prepared using the synthetic methods described in Schemes 1-15; and the examples described herein. The reference numbers of the compounds listed in Table 5 (Ex. No.) correspond to the example numbers of examples 1 to 11 described above. These data demonstrate the antiviral efficacy of the compounds of the invention as integrase inhibitors and for treatment of HIV infection and AIDS. The compounds tested display potent antiviral activity ($EC_{50}$<100 nM) and are selective cellular integrase.

Furthermore, similar antiviral activity was observed for these compounds when the HIV-1 envelope was replaced with VSV-G, validating that the compounds of the invention are post-entry inhibitors.

TABLE 5

Results of Cytoprotection-Cytotoxicity Assay

| Ex. No. | Compound | $EC_{50}$ (nM) multi-cycle |
|---|---|---|
| | L-708906 (a integrase inhibitor currently in development at Merck) | 5800 |
| | MK-0518 (Raltegravir, a marketed integrase inhibitor, brand name Isentress ™) | 20 |
| 1 | (R)-5-((3-Chloro-4-fluorophenyl)(hydroxy)methyl)-N,3-dihydroxy-4-(hydroxymethyl)picolinamide | 4 |
| 2 | 5-(4-fluorobenzyl)-N,3-dihydroxy-4-(hydroxymethyl)picolinamide | 10 |
| 3 | 5-((4-fluorophenyl)(hydroxy)methyl)-N,3-dihydroxy-4-(hydroxymethyl)picolinamide | 2 |
| 4 | 5-((4-fluorophenyl)(hydroxy)methyl)-N-hydroxy-N,2,2-trimethyl-4H-[1,3]dioxino[4,5-c]pyridine-8-carboxamide | nd |
| 5 | 5-((4-fluorophenyl)(hydroxy)methyl)-N,3-dihydroxy-4-(hydroxymethyl)-N-methylpicolinamide | 421 |
| 6 | 5-((4-fluorophenyl)(hydroxy)methyl)-3-hydroxy-4-(hydroxymethyl)-N-methoxypicolinamide | 74 |
| 7 | 5-(4-fluorobenzyl)-N,3-dihydroxy-4-methylpicolinamide | 21 |
| 8 | -((4-fluorophenyl)(hydroxy)methyl)-N,3-dihydroxy-4-methylpicolinamide | 8 |
| 9 | 5-(4-fluorobenzoyl)-N,3-dihydroxy-4-methylpicolinamide | 6678 |
| 10 | (E)-5-((4-fluorophenyl)(hydroxyimino)methyl)-N,3-dihydroxy-4-methylpicolinamide | 49 |
| 11 | (S)-5-((3-Chloro-4-fluorophenyl)(hydroxy)methyl)-N,3-dihydroxy-4-(hydroxymethyl)picolinamide | 2 |

Example 14

Effect of Protein Binding on Antiviral Activity

The multi-cycle antiviral activity in the absence and presence of human serum was determined by p24 ELISA measurement after 6 days of NL4.3 virus infection. The results, showing a moderate effect of protein binding on antiviral activity, are provided in Table 6.

TABLE 6

Effect of Protein Binding on Antiviral Activity

| | $EC_{50}$ (uM) | | |
|---|---|---|---|
| Compound | 10% FBS | 10% FBS + 40% HS | Fold-change with HS |
| Raltegravir | 0.047 | 0.064 | 1.4 |
| Example 1 | 0.006 | 0.006 | 1 |
| Example 11 | 0.001 | 0.001 | 1 |

Other Embodiments

The examples, synthetic schemes and procedures provided herein are for the purpose of illustration only. They are not intended to be exhaustive or to limit the scope of the invention to the specific examples, synthetic schemes, and procedures described herein. Although the invention has been described with reference to several embodiments, it will be understood by one of ordinary skill in the art that various modifications can be made without departing from the spirit and the scope of the invention, as set forth in the claims. Other embodiments are in the claims.

What is claimed is:

1. A method of treating an HIV infection in a mammal, said method comprising administering to said mammal a compound in an amount effective for the treatment of said HIV infection, wherein said compound is selected from the group consisting of:

(i) a compound of formula I,

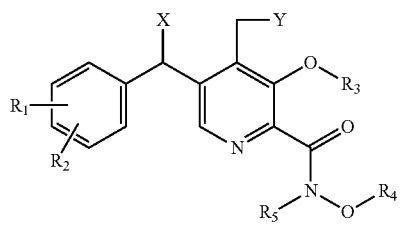

wherein:
X is H or OH;
Y is H or OH;
$R_1$ is H or halogen (F, Cl, Br, I);
$R_2$ is H or halogen (F, Cl, Br, I);
$R_3$ is H, $C_{1-6}$ alkyl, $C_{1-6}$ fluoroalkyl, or benzyl;
$R_4$ is H, $C_{1-6}$ alkyl, or benzyl; and
$R_5$ is H or $C_{1-6}$ alkyl; or pharmaceutically acceptable salts or solvates thereof;

(ii) a compound of formula Ic,

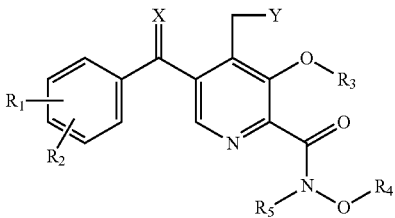

wherein:
X is O or N—OH;
Y is H or OH;
$R_1$ is H or halogen (F, Cl, Br, I);
$R_2$ is H or halogen (F, Cl, Br, I);
$R_3$ is H, $C_{1-6}$ alkyl or benzyl;
$R_4$ is H, $C_{1-6}$ alkyl or benzyl; and
$R_5$ is H or $C_{1-6}$ alkyl; or
pharmaceutically acceptable salts thereof; and (iii) a compound selected from the group consisting of:
(R)-5-((3-chloro-4-fluorophenyl)(hydroxy)methyl)-N,3-dihydroxy-4-(hydroxymethyl)picolinamide;
5-(4-fluorobenzyl)-N,3-dihydroxy-4-(hydroxymethyl)picolinamide;
5-((4-fluorophenyl)(hydroxy)methyl)-N,3-dihydroxy-4-(hydroxymethyl)picolinamide;
5-((4-fluorophenyl)(hydroxy)methyl)-N-hydroxy-N,2,2-trimethyl-4H-[1,3]dioxino[4,5-c]pyridine-8-carboxamide;
5-((4-fluorophenyl)(hydroxy)methyl)-N,3-dihydroxy-4-(hydroxymethyl)-N-methylpicolinamide;
5-((4-fluorophenyl)(hydroxy)methyl)-3-hydroxy-4-(hydroxymethyl)-N-methoxypicolinamide;
5-(4-fluorobenzyl)-N,3-dihydroxy-4-methylpicolinamide;
5-((4-fluorophenyl)(hydroxy)methyl)-N,3-dihydroxy-4-methylpicolinamide;
5-(4-fluorobenzoyl)-N,3-dihydroxy-4-methylpicolinamide;

(E)-5-((4-fluorophenyl)(hydroxyimino)methyl)-N,3-dihydroxy-4-methylpicolinamide; and
(S)-5-((3-chloro-4-fluorophenyl)(hydroxy)methyl)-N,3-dihydroxy-4-(hydroxymethyl)picolinamide; or pharmaceutically acceptable salts thereof.

2. A method of treating AIDS or AIDS-related complex in a mammal, said method comprising administering to said mammal a compound in an amount effective for the treatment of said AIDS or AIDS-related complex,
wherein said compound is selected from the group consisting of:
(i) a compound of formula I,

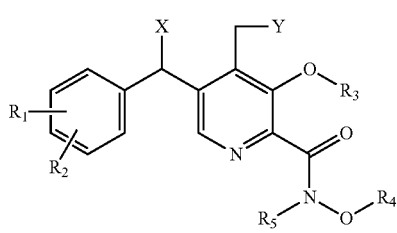

wherein:
X is H or OH;
Y is H or OH;
$R_1$ is H or halogen (F, Cl, Br, I);
$R_2$ is H or halogen (F, Cl, Br, I);
$R_3$ is H, $C_{1-6}$ alkyl, $C_{1-6}$ fluoroalkyl, or benzyl;
$R_4$ is H, $C_{1-6}$ alkyl, or benzyl; and
$R_5$ is H or $C_{1-6}$ alkyl; or pharmaceutically acceptable salts thereof;
(ii) a compound of formula Ic,

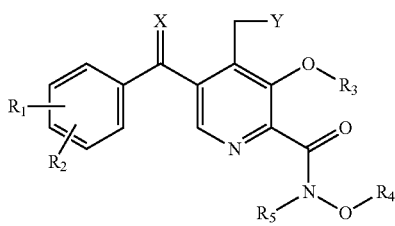

wherein:
X is O or N—OH;
Y is H or OH;
$R_1$ is H or halogen (F, Cl, Br, I);
$R_2$ is H or halogen (F, Cl, Br, I);
$R_3$ is H, $C_{1-6}$ alkyl or benzyl;
$R_4$ is H, $C_{1-6}$ alkyl or benzyl; and
$R_5$ is H or $C_{1-6}$ alkyl; or
pharmaceutically acceptable salts thereof; and
(iii) a compound selected from the group consisting of:
(R)-5-((3-chloro-4-fluorophenyl)(hydroxy)methyl)-N,3-dihydroxy-4-(hydroxymethyl)picolinamide;
5-(4-fluorobenzyl)-N,3-dihydroxy-4-(hydroxymethyl)picolinamide;
5-((4-fluorophenyl)(hydroxy)methyl)-N,3-dihydroxy-4-(hydroxymethyl)picolinamide;
5-((4-fluorophenyl)(hydroxy)methyl)-N-hydroxy-N,2,2-trimethyl-4H-[1,3]dioxino[4,5-c]pyridine-8-carboxamide;
5-((4-fluorophenyl)(hydroxy)methyl)-N,3-dihydroxy-4-(hydroxymethyl)-N-methylpicolinamide;
5-((4-fluorophenyl)(hydroxy)methyl)-3-hydroxy-4-(hydroxymethyl)-N-methoxypicolinamide;
5-(4-fluorobenzyl)-N,3-dihydroxy-4-methylpicolinamide;
5-((4-fluorophenyl)(hydroxy)methyl)-N,3-dihydroxy-4-methylpicolinamide;
5-(4-fluorobenzoyl)-N,3-dihydroxy-4-methylpicolinamide;
(E)-5-((4-fluorophenyl)(hydroxyimino)methyl)-N,3-dihydroxy-4-methylpicolinamide; and
(S)-5-((3-chloro-4-fluorophenyl)(hydroxy)methyl)-N,3-dihydroxy-4-(hydroxymethyl)picolinamide; or pharmaceutically acceptable salts or solvates thereof.

3. A method of inhibiting HIV replication in a mammal, said method comprising administering to said mammal a compound in an amount effective to inhibit HIV replication in a mammal,
wherein said compound is selected from the group consisting of:
(i) a compound of formula I,

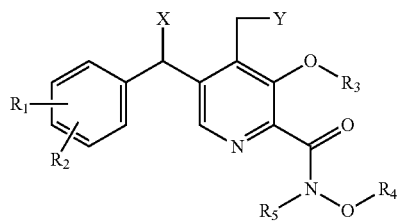

wherein:
X is H or OH;
Y is H or OH;
$R_1$ is H or halogen (F, Cl, Br, I);
$R_2$ is H or halogen (F, Cl, Br, I);
$R_3$ is H, $C_{1-6}$ alkyl, $C_{1-6}$ fluoroalkyl, or benzyl;
$R_4$ is H, $C_{1-6}$ alkyl, or benzyl; and
$R_5$ is H or $C_{1-6}$ alkyl; or pharmaceutically acceptable salts or solvates thereof;
(ii) a compound of formula Ic,

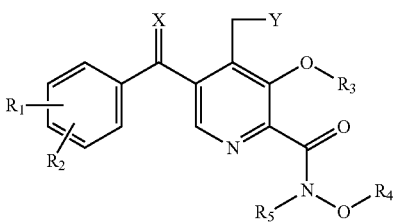

wherein:
X is O or N—OH;
Y is H or OH;
$R_1$ is H or halogen (F, Cl, Br, I);
$R_2$ is H or halogen (F, Cl, Br, I);
$R_3$ is H, $C_{1-6}$ alkyl or benzyl;
$R_4$ is H, $C_{1-6}$ alkyl or benzyl; and
$R_5$ is H or $C_{1-6}$ alkyl; or
pharmaceutically acceptable salts or solvates thereof; and (iii) a compound selected from the group consisting of:
(R)-5-((3-chloro-4-fluorophenyl)(hydroxy)methyl)-N, 3-dihydroxy-4-(hydroxymethyl)picolinamide;
5-(4-fluorobenzyl)-N,3-dihydroxy-4-(hydroxymethyl)picolinamide;
5-((4-fluorophenyl)(hydroxy)methyl)-N,3-dihydroxy-4-(hydroxymethyl)picolinamide;
5-((4-fluorophenyl)(hydroxy)methyl)-N-hydroxy-N,2,2-trimethyl-4H-[1,3]dioxino[4,5-c]pyridine-8-carboxamide;
5-((4-fluorophenyl)(hydroxy)methyl)-N,3-dihydroxy-4-(hydroxymethyl)-N-methylpicolinamide;
5-((4-fluorophenyl)(hydroxy)methyl)-3-hydroxy-4-(hydroxymethyl)-N-methoxypicolinamide;
5-(4-fluorobenzyl)-N,3-dihydroxy-4-methylpicolinamide;
5-((4-fluorophenyl)(hydroxy)methyl)-N,3-dihydroxy-4-methylpicolinamide;
5-(4-fluorobenzoyl)-N,3-dihydroxy-4-methylpicolinamide;
(E)-5-((4-fluorophenyl)(hydroxyimino)methyl)-N,3-dihydroxy-4-methylpicolinamide; and
(S)-5-((3-chloro-4-fluorophenyl)(hydroxy)methyl)-N, 3-dihydroxy-4-(hydroxymethyl)picolinamide; or
pharmaceutically acceptable salts thereof.

4. The method of claim 3, wherein said HIV is resistant to at least one HIV inhibiting agent.

5. The method of claim 1, wherein the compound of formula I is selected from the group consisting of:
(i) a compound of formula Ia,

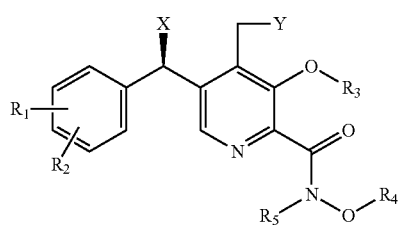

wherein X is OH; and $R_3$ is H, $C_{1-6}$ alkyl or benzyl; or pharmaceutically acceptable salts thereof;
(ii) a compound of formula Ib,

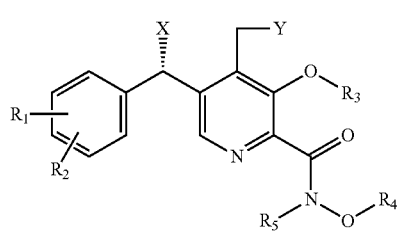

wherein X is OH; and $R_3$ is H, $C_{1-6}$ alkyl or benzyl; or pharmaceutically acceptable salts thereof; and
(iii) a compound selected from the group consisting of:
(R)-5-((3-chloro-4-fluorophenyl)(hydroxy)methyl)-N, 3-dihydroxy-4-(hydroxymethyl)picolinamide;
5-(4-fluorobenzyl)-N,3-dihydroxy-4-(hydroxymethyl)picolinamide; and
(S)-5-((3-chloro-4-fluorophenyl)(hydroxy)methyl)-N, 3-dihydroxy-4-(hydroxymethyl)picolinamide; or
pharmaceutically acceptable salts thereof.

6. The method of claim 2, wherein the compound of formula I is selected from the group consisting of:
(I) a compound of formula Ia,

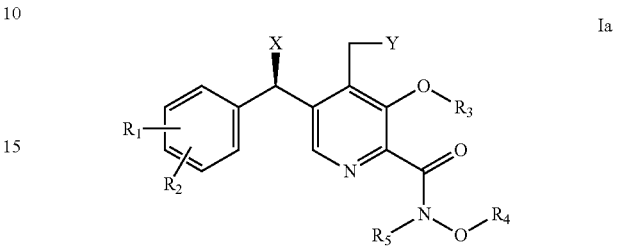

wherein X is OH; and $R_3$ is H, $C_{1-6}$ alkyl or benzyl; or pharmaceutically acceptable salts thereof;
(ii) a compound of formula Ib,

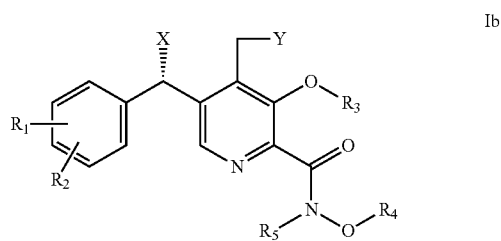

wherein X is OH; and $R_3$ is H, $C_{1-6}$ alkyl or benzyl; or pharmaceutically acceptable salts thereof; and
(iii) a compound selected from the group consisting of:
(R)-5-((3-chloro-4-fluorophenyl)(hydroxy)methyl)-N, 3-dihydroxy-4-(hydroxymethyl)picolinamide;
5-(4-fluorobenzyl)-N,3-dihydroxy-4-(hydroxymethyl)picolinamide; and
(S)-5-((3-chloro-4-fluorophenyl)(hydroxy)methyl)-N, 3-dihydroxy-4-(hydroxymethyl)picolinamide; or
pharmaceutically acceptable salts thereof.

7. The method of claim 3, wherein the compound of formula I is selected from the group consisting of:
(i) a compound of formula Ia,

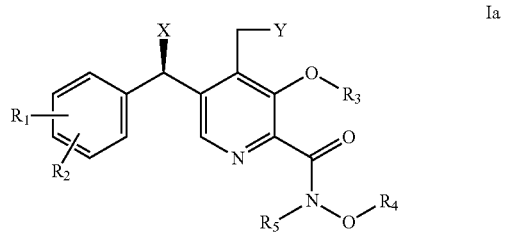

wherein X is OH; and $R_3$ is H, $C_{1-6}$ alkyl or benzyl; or pharmaceutically acceptable salts thereof;

(ii) a compound of formula Ib,

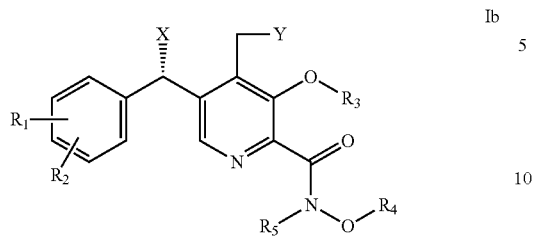

wherein X is OH; and $R_3$ is H, $C_{1-6}$ alkyl or benzyl; or pharmaceutically acceptable salts thereof; and (iii) a compound selected from the group consisting of:
- (R)-5-((3-chloro-4-fluorophenyl)(hydroxy)methyl)-N,3-dihydroxy-4-(hydroxymethyl)picolinamide;
- 5-(4-fluorobenzyl)-N,3-dihydroxy-4-(hydroxymethyl)picolinamide; and
- (S)-5-((3-chloro-4-fluorophenyl)(hydroxy)methyl)-N,3-dihydroxy-4-(hydroxymethyl)picolinamide; or pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 8,664,248 B2 | Page 1 of 1 |
| APPLICATION NO. | : 13/605502 | |
| DATED | : March 4, 2014 | |
| INVENTOR(S) | : Brent Richard Stranix et al. | |

It is certified that error appears in the above-identified patent and that said Letters Patent is hereby corrected as shown below:

In the Claims

Column 40, Claim 1, Line 24, replace "salts or solvates thereof;" with --salts thereof;--.

Column 42, Claim 2, Line 15, replace "salts or solvates thereof." with --salts thereof.--;

Claim 3, Line 44, replace "salts or solvates thereof;" with --salts thereof;--;

Line 66, replace "salts or solvates thereof;" with --salts thereof;--.

Signed and Sealed this
Third Day of June, 2014

Michelle K. Lee
*Deputy Director of the United States Patent and Trademark Office*